United States Patent
Coates

(10) Patent No.: US 10,724,010 B2
(45) Date of Patent: Jul. 28, 2020

(54) RECOMBINANTLY ENGINEERED CELLS EXPRESSING CHLORITE DISMUTASE AND METHODS FOR USING SAME IN CELL CULTURE

(71) Applicant: The Regents of the University of California, Oakland, CA (US)

(72) Inventor: John D. Coates, Walnut Creek, CA (US)

(73) Assignee: The Regents of the Uniiversity of California, Oakland, CA (US)

(*) Notice: Subject to any disclaimer, the term of this patent is extended or adjusted under 35 U.S.C. 154(b) by 426 days.

(21) Appl. No.: 15/101,267

(22) PCT Filed: Dec. 5, 2014

(86) PCT No.: PCT/US2014/068842
§ 371 (c)(1),
(2) Date: Jun. 2, 2016

(87) PCT Pub. No.: WO2015/085199
PCT Pub. Date: Jun. 11, 2015

(65) Prior Publication Data
US 2017/0029788 A1  Feb. 2, 2017

Related U.S. Application Data

(60) Provisional application No. 61/912,487, filed on Dec. 5, 2013.

(51) Int. Cl.
| | | |
|---|---|---|
| *C12N 9/02* | (2006.01) | |
| *C12N 1/20* | (2006.01) | |
| *C12N 1/38* | (2006.01) | |
| *C12N 13/00* | (2006.01) | |
| *C12P 7/06* | (2006.01) | |
| *C12P 7/16* | (2006.01) | |
| *C12P 7/28* | (2006.01) | |

(52) U.S. Cl.
CPC ............ *C12N 9/0069* (2013.01); *C12N 1/20* (2013.01); *C12N 1/38* (2013.01); *C12N 13/00* (2013.01); *C12P 7/065* (2013.01); *C12P 7/16* (2013.01); *C12P 7/28* (2013.01); *C12Y 113/11049* (2013.01); *Y02E 50/17* (2013.01)

(58) Field of Classification Search
None
See application file for complete search history.

(56) References Cited

U.S. PATENT DOCUMENTS

| | | |
|---|---|---|
| 5,891,339 A | 4/1999 | Van Ginkel et al. |
| 2014/0134736 A1* | 5/2014 | Coates .................. C07K 14/195 435/455 |

FOREIGN PATENT DOCUMENTS

WO    WO-2012/166964 A1    12/2012

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10: 8-9.*
Goblirsch et al. Journal of Molecular biology (2011), 408:379-398.*
Mullerat et al. J. Food protection, (1994), 57(7): 596-603.*
International Search Report and Written Opinion Received for PCT Patent Application No. PCT/US2014/068842 dated Mar. 27, 2015, 12 pages.
Bichai et al., "Assessing the Disinfecting Power of Chlorite in Drinking Water", Water Qual. Res. J. Canada, vol. 41, No. 4, 2006, pp. 375-382.
Heinemann et al., "The biochemistry of heme biosynthesis", Archives of Biochemistry and Biophysics, vol. 474, No. 2, 2008, pp. 238-251.
Los et al., "Bacteriophage contamination: is there a simple method to reduce its deleterious effects in laboratory cultures and biotechnological factories?", J. Appl. Genet, vol. 45, No. 1, 2004, pp. 111-120.
Streit et al., "Chemical and Steady-State Kinetic Analyses of a Heterologously Expressed Heme Dependent Chlorite Dismutase", Biochemistry, vol. 47, No. 19, 2008, pp. 5271-5280.

* cited by examiner

*Primary Examiner* — Iqbal H Chowdhury
(74) *Attorney, Agent, or Firm* — Richard Aron Osman

(57) ABSTRACT

The present disclosure relates to recombinantly engineered cells that contain a chlorite dismutase polypeptide and methods for culturing such cells in a culture medium containing chlorite in an amount sufficient to reduce the growth rate or kill contaminating microorganisms without killing the recombinantly engineered cells. Also provided are methods for the production of a fermentation product using the recombinantly engineered cells.

20 Claims, 11 Drawing Sheets

RECOMBINANTLY ENGINEERED CELLS EXPRESSING CHLORITE DISMUTASE AND METHODS FOR USING SAME IN CELL CULTURE

CROSS REFERENCES TO RELATED APPLICATIONS

This application is a U.S. National Stage application of PCT/US2014/068842, filed internationally on Dec. 5, 2014, which claims the priority benefit of U.S. Provisional Application Ser. No. 61/912,487, filed Dec. 5, 2013, which are incorporated herein by reference in their entireties.

FIELD OF THE INVENTION

The present disclosure relates to recombinantly engineered cells containing a chlorite dismutase polypeptide, and methods of using such cells for culturing in a medium treated with chlorite to reduce the growth rate or kill contaminating microorganisms. The methods and compositions described herein may further be used to produce a fermentation product, such as a hydrocarbon, a hydrocarbon derivative, ethanol, or butanol.

BACKGROUND

Methods to manufacture fuels and other value-added chemicals through industrial biotechnology have the potential to improve these important industries by introducing greener and more sustainable processes. The use of biotechnologies to manufacture fuels and value-added chemicals can reduce the generation of waste and carbon dioxide emissions while improving energy efficiency, as compared to using fossil fuels (Tang, W. L. and Zhao, H. (2009). Biotechnol J 4(12): 1725-39). Industrial biotechnology also represents a growing market; the World Economic Forum estimates that the revenue potential for bio-based energy, fuels, chemicals, and materials by the year 2020 is nearly $300 billion. New biotechnological advances are constantly expanding the capabilities of engineered biological systems to produce useful products.

One problem common to all biotechnological processes is hygiene. Biological contamination in industrial fermentation processes constitutes one of the most devastating threats to the productivity of the biotechnology facilities. There are several types of infections that can occur, including eukaryotic, prokaryotic, and bacteriophage. These infections are usually the result of poor process hygiene, whether they are due to operator failure or simply the impossible logistics associated with large scale processes. For example, due to global bacteriophage abundance, bioprocesses based on bacterial activities are in constant threat of bacteriophage infections (Los et al. (2004). J Appl Genet 45(1): 111-20).

With the planned development of industrial, fermentation-based biofuel production, the scale of bioprocesses is moving beyond anything previously conceived. Thus, there exists a need for improving hygienic methods for culturing cells and producing fermentation products.

BRIEF SUMMARY

In order to meet this need, the present disclosure provides methods and compositions for engineering a cell to express a chlorite dismutase polypeptide, and culturing the cell in the presence of chlorite in an amount sufficient to kill contaminating microorganisms while not killing the cultured cell. In one aspect, these methods and compositions are useful in improving industrial fermentation hygiene where the cultured cell produces a fermentation product, e.g., a hydrocarbon, hydrocarbon derivative, ethanol, or butanol. Moreover, the present disclosure is based at least in part on the surprising discovery that chlorite dismutase, a metabolic enzyme endogenously utilized by perchlorate reducing bacteria, can protect a host cell from the toxic effects of a chlorite-containing disinfectant.

Accordingly, certain aspects of the present disclosure relate to a method of culturing a cell, by: a) culturing a recombinantly engineered cell containing a chlorite dismutase polypeptide in a culture medium under conditions whereby the chlorite dismutase polypeptide is expressed in the cell, where the culture medium may also include one or more contaminating microorganisms; and b) treating the culture medium with chlorite in an amount sufficient to reduce the growth rate or kill the one or more contaminating microorganisms without killing the cell, thereby culturing the cell.

In certain embodiments, the culture medium is treated with chlorite prior to culturing the cell. In certain embodiments, the chlorite is produced in the culture medium by electrochemical generation. In certain embodiments, the method further includes prior to step (a), adding the cell to the culture medium. In certain embodiments, the chlorite is added to the culture medium concurrently with the addition of the cell to the culture medium. In certain embodiments, the culture medium is treated with the chlorite intermittently. In certain embodiments, the method further includes growing the cell in a bioreactor. In certain embodiments, the culture medium containing the cell is treated with chlorite prior to growing the cell in the bioreactor. In certain embodiments, the culture medium containing the cell is treated with chlorite while growing the cell in the bioreactor. In certain embodiments that may be combined with any of the preceding embodiments, the cell is a bacterial cell, a yeast cell, or a fungal cell. In certain embodiments that may be combined with any of the preceding embodiments, the cell is a bacterial cell. In certain embodiments that may be combined with any of the preceding embodiments, the bacterial cell is a *Clostridium* cell. In certain embodiments that may be combined with any of the preceding embodiments, the cell is a yeast cell. In certain embodiments, the cell is an animal cell. In certain embodiments, the animal cell is a mammalian or insect cell. In certain embodiments that may be combined with any of the preceding embodiments, the cell does not endogenously express a chlorite dismutase. In certain embodiments that may be combined with any of the preceding embodiments, the chlorite dismutase polypeptide is derived from a perchlorate reducing bacterium. In certain embodiments that may be combined with any of the preceding embodiments, the chlorite dismutase polypeptide is at least 25%, 30%, 35%, 40%, 45%, 50%, 55%, 60%, 65%, 70%, 75%, 80%, 85%, 90%, 95%, 99%, or 100% identical to a chlorite dismutase polypeptide having a RefSeq accession number selected from YP_005026408.1, YP_285781.1, AAM92878.1, WP_014235269.1, AAT07043.1, WP_009867516.1, CAC14884.1, WP_013516316.1, ACA21503.1, YP_004267835.1, EFH80711.1, YP_004178041.1, YP_004367213.1, YP_004058724.1, and YP_004172359.1. In certain embodiments that may be combined with any of the preceding embodiments, the cell further contains the proteins necessary to produce a fermentation product. In certain embodiments that may be combined with any of the preceding embodiments, the cell is further recombinantly engineered to express one or more of the proteins necessary to produce a fermentation product. In certain embodiments that may be combined with any of the preceding embodiments, the method further includes culturing the cell under conditions sufficient for the cell to produce a fermentation product. In certain embodiments that may be combined with any of the preceding embodiments, the fermentation product is a hydrocarbon or hydrocarbon derivative. In certain embodiments, the hydrocarbon or hydrocarbon derivative contains ethanol or butanol. In certain embodiments that may be combined with any of the preceding embodiments, the cell further contains one or more proteins necessary for heme biosynthesis. In certain embodiments, the cell is further recombinantly engineered to express the one or more of the proteins necessary for heme biosynthesis. In certain embodiments that may be combined with any of the preceding embodiments, the one or more proteins necessary for heme biosynthesis are selected from uroporphyrinogen III decarboxylase, coproporphyrinogen III oxidase, protoporphyrinogen IX oxidase, and ferrochelatase. In certain embodiments that may be combined with any of the preceding embodiments, the one or more contaminating microorganisms are selected from prokaryotic microorganisms, bacteria, archaea, eukaryotic microorganisms, fungal cells, yeast, algae, and bacteriophages. In certain embodiments that may be combined with any of the preceding embodiments, the one or more contaminating microorganisms are bacteria. In certain embodiments, the bacteria are selected from *Lactobacillus, Clostridium, Pediococcus, Enterococcus, Acetobacter*, and *Gluconobacter*. In certain embodiments that may be combined with any of the preceding embodiments, the one or more contaminating microorganisms are bacteriophages.

Other aspects of the present disclosure relate to a recombinantly engineered cell containing a chlorite dismutase polypeptide.

In certain embodiments, the cell is a bacterial cell, a yeast cell, or a fungal cell. In certain embodiments, the cell is an animal cell. In certain embodiments, the animal cell is a mammalian or insect cell. In certain embodiments that may be combined with any of the preceding embodiments, the cell does not endogenously express a chlorite dismutase. In certain embodiments that may be combined with any of the preceding embodiments, the chlorite dismutase polypeptide is derived from a perchlorate reducing bacterium. In certain embodiments that may be combined with any of the preceding embodiments, the chlorite dismutase polypeptide is at least 25%, 30%, 35%, 40%, 45%, 50%, 55%, 60%, 65%, 70%, 75%, 80%, 85%, 90%, 95%, 99%, or 100% identical to a chlorite dismutase polypeptide having a RefSeq accession number selected from YP_005026408.1, YP_285781.1, AAM92878.1, WP_014235269.1, AAT07043.1, WP_009867516.1, CAC14884.1, WP_013516316.1, ACA21503.1, YP_004267835.1, EFH80711.1, YP_004178041.1, YP_004367213.1, YP_004058724.1, and YP_004172359.1. In certain embodiments that may be combined with any of the preceding embodiments, the chlorite dismutase polypeptide is expressed under the control of a constitutive promoter. In certain embodiments that may be combined with any of the preceding embodiments, the chlorite dismutase polypeptide is expressed under the control of an inducible promoter. In certain embodiments that may be combined with any of the preceding embodiments, the cell further contains the proteins necessary to produce a fermentation product. In certain embodiments that may be combined with any of the preceding embodiments, the cell is further recombinantly engineered to express one or more of the proteins necessary to produce a fermentation product. In certain embodiments that may be combined with any of the preceding embodiments, the fermentation product is a hydrocarbon or hydrocarbon derivative. In certain embodiments that may be combined with any of the preceding embodiments, the hydrocarbon or hydrocarbon derivative contains ethanol or butanol. In certain embodiments that may be combined with any of the preceding embodiments, the cell further contains one or more proteins necessary for heme biosynthesis. In certain embodiments, the cell is further recombinantly engineered to express the one or more of the proteins necessary for heme biosynthesis. In certain embodiments that may be combined with any of the preceding embodiments, the one or more proteins necessary for heme biosynthesis are selected from uroporphyrinogen III decarboxylase, coproporphyrinogen III oxidase, protoporphyrinogen IX oxidase, and ferrochelatase.

Other aspects of the present disclosure relate to a culture medium containing the cell of any of the preceding embodiments. In certain embodiments, the culture further includes chlorite ions. In certain embodiments, the chlorite ions are at a concentration sufficient to kill one or more microorganisms with which the cell is susceptible to contamination.

DETAILED DESCRIPTION

Figure 1:
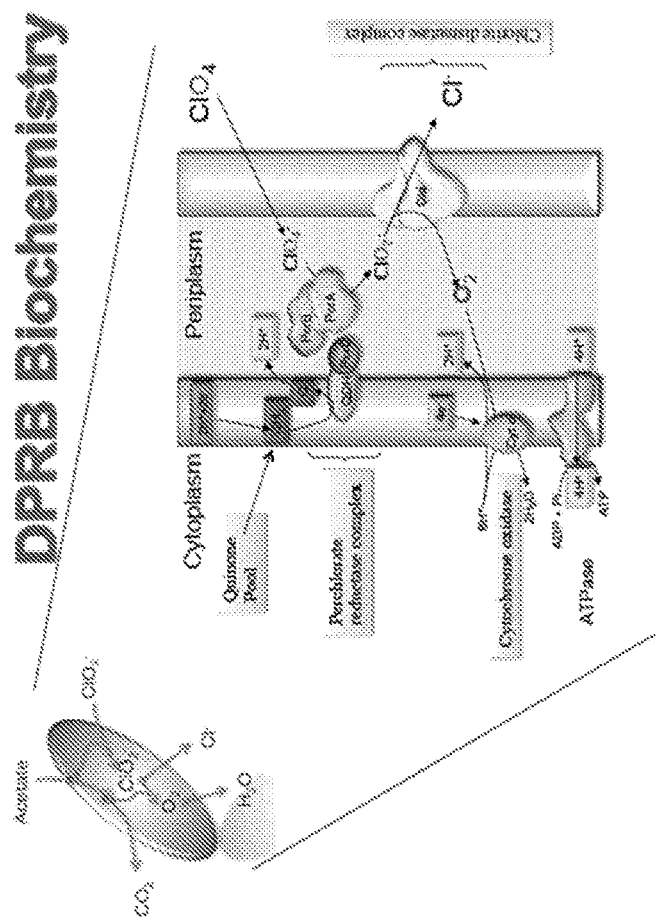
FIG. 1 depicts a model of the respiratory pathway of perchlorate reduction in perchlorate reducing bacteria.

The following description sets forth exemplary methods, parameters and the like. It should be recognized, however, that such description is not intended as a limitation on the scope of the present disclosure but is instead provided as a description of exemplary embodiments.

The present disclosure relates generally to methods of culturing a cell, whereby the cell is recombinantly engineered to express a chlorite dismutase polypeptide and where the culture medium containing the cell is treated with chlorite dismutase to reduce the growth rate or kill contaminating microorganisms without killing the cultured cell. Further embodiments relate generally to the use of this method for the generation of a fermentation product. The present disclosure also relates to compositions including a cell recombinantly engineered to express a chlorite dismutase polypeptide. It also relates to compositions including a culture medium that contains a cell recombinantly engineered to express a chlorite dismutase polypeptide.

In particular, the present disclosure is based, at least in part, on the surprising discovery that a host cell recombinantly engineered to express chlorite dismutase is protected from the toxic effects of chlorite by the activity of the chlorite dismutase. Furthermore, by recombinantly engineering a cell that would not normally express chlorite dismutase to express such an enzyme, the cell is surprisingly able to grow in culture medium containing a concentration of chlorite that would, without chlorite dismutase expression, kill the cell, prevent or slow its growth. Since chlorite is a common component in many disinfecting solutions, adding chlorite to culture medium containing a cell recombinantly engineered to express chlorite dismutase allows the recombinant cell to grow while reducing the growth, or killing, contaminating microorganisms.

Accordingly, the present disclosure provides methods and compositions for culturing a cell that is recombinantly engineered to express a chlorite dismutase in the presence of chlorite in an amount sufficient to reduce the growth rate or kill additional contaminating microorganism(s) without killing the recombinantly engineered cell. Further methods and compositions are provided for culturing the recombinantly engineered cell where the cell is also recombinantly engineered to produce a fermentation product. These methods and compositions allow the biological production of important fuels and other commodity chemicals with an improved level of process sanitation by reducing the growth rate or killing contaminating microorganisms without interfering with the recombinant cells generating a product.

Chlorite Dismutase

Certain aspects of the present disclosure relate to a cell that is recombinantly engineered to express a chlorite dismutase polypeptide. As used herein, "chlorite dismutase" (used interchangeably with "chlorite dismutase polypeptide") refers to an enzyme that catalyzes the reaction converting chlorite ($ClO_2^-$) into chloride ($Cl^-$) and oxygen ($O_2$). The term "chlorite O(2)-lyase" may also be used interchangeably. The EC classification for chlorite dismutase is EC 1.13.11.49. In the present disclosure, any enzyme demonstrated or predicted to have the activity corresponding to EC classification 1.13.11.49 is considered to be a chlorite dismutase polypeptide. The GO term ID for chlorite dismutase is GO: 0050587. In the present disclosure, any protein demonstrated or predicted to have the cellular component, biological process, or molecular function corresponding to the GO term ID GO: 0050587 is considered to be a chlorite dismutase polypeptide. The Pfam protein family for chlorite dismutase is PF06778. In the present disclosure, any protein annotated to belong to the family corresponding to the Pfam classification PF06778 is considered to be a chlorite dismutase polypeptide.

The active site of a chlorite dismutase contains a heme group. The active enzyme is a multimeric complex of chlorite dismutase monomers, and enzymes have been purified with different amounts of multimers, from two to six monomers per complex. Enzymatically, chlorite dismutase is highly unique. Chlorite dismutase is one of only four known enzymatic systems able to catalyze covalent O—O bond formation (Bardiya N and Bae J H (2011). Microbiol Res 166(4):237-54). The amino acid sequence of chlorite dismutase is also highly distinctive. For example, no other enzyme is more than 24% similar to the *D. agitata* chlorite dismutase (Bender et al. (2002). Appl Environ Microbiol 68(10):4820-6).

The active site of a chlorite dismutase contains a heme group. The active enzyme is a multimeric complex of chlorite dismutase monomers, and enzymes have been purified with different amounts of multimers, from two to six monomers per complex. Enzymatically, chlorite dismutase is highly unique. The amino acid sequence of chlorite dismutase is also highly distinctive; for example, no other enzyme is more than 24% similar to the *D. agitata* chlorite dismutase (Bender et al. (2002). Appl Environ Microbiol 68(10):4820-6).

Without wishing to be bound by theory, it is believed that chlorite is a strong oxidizing agent that is highly reactive and has antimicrobial and antiviral effects due to its oxidation of cell membrane components or viral proteins, leading to cell lysis or denaturation of viral proteins. Chloride ions, by contrast, are non-reactive and harmless. Chloride ions are used for a variety of cellular processes: e.g., regulation of pH and organic solute transport through chloride channel proteins. In some embodiments, chlorite dismutase polypeptides of the present disclosure can localize to the outer cell membrane of a host cell of the present disclosure. Without wishing to be bound to theory, the expression of chlorite dismutase on the outer membrane of a cell is thought to enable the cell to convert harmful chlorite anions present in a culture medium into harmless chloride and oxygen before the chlorite is able to oxidize cellular components and reduce the growth rate or kill the cell. In some embodiments, the present disclosure employs chlorite dismutase activity to demonstrate a detoxification function that may be utilized through recombinant engineering to improve culturing processes, such as fermentation sanitation, among other applications.

In some embodiments, suitable chlorite dismutase polypeptides of the present disclosure may be obtained from perchlorate reducing bacteria. "Perchlorate reducing bacteria," or "PRB," as used herein refers to any prokaryotic microorganism that possesses an endogenous capability of metabolizing a (per)chlorate anion into chloride. All known PRBs contain a gene encoding a chlorite dismutase polypeptide. Chlorite dismutase polypeptides have been found in at least 13 bacterial and 3 archaeal phyla (Goblirsch, B. et al. J Mol Biol 408(3):379-98 (2011)), and over 50 PRB species have been isolated (Coates, J. D. & Achenbach, L. A. Nat Rev Micro 2, 569-580 (2004)). In addition, several non-PRB species have also been found to contain a chlorite dismutase polypeptide. All known PRBs are facultative anaerobes or microaerophilic. They represent a phylogenetically diverse set of microorganisms within the phylum of Proteobacteria. PRBs have been found in both natural and human-contaminated environments, including soil, hot springs, wastewater treatment plants, animal waste lagoons, and even *Antarctica* (Coates, J. D. & Achenbach, L. A. Nat Rev Micro 2, 569-580 (2004); Bardiya N and Bae J H (2011). Microbiol Res 166(4):237-54). PRBs use perchlorate or chlorate reduction as part of their endogenous respiration, completely oxidizing an organic carbon source (most commonly acetate but sugars, lactate, pyruvate and others have been described) to generate carbon dioxide and water. In this process, (per)chlorate is used as an electron acceptor. All of the genes necessary for (per)chlorate reduction, including the enzymatic components, accessory components, and regulatory components, are encoded by genes clustered together on a highly conserved perchlorate reduction genomic island (PRI) in perchlorate reducing microorganisms or a chlorate reduction composite transposon interior (CRI) in chlorate reducing microorganisms that are thought to have spread among these organisms through horizontal gene transfer (Melnyk R A et al. (2011). Appl Environ Microbiol 77(20): 7401-4; Clark I C et al. (2013) mBio 4:e00379-13).

Examples of suitable chlorite dismutase polypeptides include, without limitation, those listed in Table 1, and homologs thereof.

TABLE 1

| NCBI GI Accession Number | NCBI RefSeq Accession Number |
|---|---|
| 372486843 | YP_005026408.1 |
| 71908194 | YP_285781.1 |
| 504001275 | WP_014235269.1 |
| 22212277 | AAM92878.1 |
| 11121510 | CAC14884.1 |
| 46948122 | AAT07043.1 |
| 168203360 | ACA21503.1 |
| 325106767 | YP_004267835.1 |
| 320102450 | YP_004178041.1 |
| 328949878 | YP_004367213.1 |
| 313680985 | YP_004058724.1 |
| 320335648 | YP_004172359.1 |
| 161723183 | NP_244692.2 |
| 10176450 | BAB07544.1 |
| 161511066 | NP_391647.2 |
| 384177417 | YP_005558802.1 |
| 350268047 | YP_004879354.1 |
| 221311731 | ZP_03593578.1 |
| 321313325 | YP_004205612.1 |
| 398305248 | ZP_10508834.1 |
| 398308738 | ZP_10512212.1 |
| 296331406 | ZP_06873878.1 |
| 57866176 | YP_187831.1 |
| 394231816 | EJD77439.1 |
| 394250268 | EJD95462.1 |
| 365225074 | EHM66327.1 |

TABLE 1-continued

| NCBI GI Accession Number | NCBI RefSeq Accession Number |
|---|---|
| 27467276 | NP_763913.1 |
| 394237370 | EJD82862.1 |
| 242241926 | ZP_04796371.1 |
| 251810009 | ZP_04824482.1 |
| 365231827 | EHM72844.1 |
| 374820240 | EHR84334.1 |
| 319650951 | ZP_08005086.1 |
| 52082283 | YP_081074.1 |
| 387591609 | EIJ83926.1 |
| 288554459 | YP_003426394.1 |
| 294501915 | YP_003565615.1 |
| 384044252 | YP_005492269.1 |
| 295707263 | YP_003600338.1 |
| 394284803 | EJE28902.1 |
| 154687885 | YP_001423046.1 |
| 384267298 | YP_005423005.1 |
| 389572462 | ZP_10162547.1 |
| 242372811 | ZP_04818385.1 |
| 373855300 | ZP_09598046.1 |
| 387928340 | ZP_10131018.1 |
| 384161381 | YP_005543454.1 |
| 149182787 | ZP_01861250.1 |
| 384166285 | YP_005547664.1 |
| 308175490 | YP_003922195.1 |
| 314932813 | ZP_07840182.1 |
| 223043041 | ZP_03613089.1 |
| 194016490 | ZP_03055104.1 |
| 157694165 | YP_001488627.1 |
| 341596274 | EGS38890.1 |
| 311070287 | YP_003975210.1 |
| 205375386 | ZP_03228175.1 |
| 341843773 | EGS84994.1 |
| 365156917 | ZP_09353202.1 |
| 49482817 | YP_040041.1 |
| 341842114 | EGS83547.1 |
| 57651462 | YP_185518.1 |
| 253732974 | ZP_04867139.1 |
| 258422774 | ZP_05685677.1 |
| 15923577 | NP_371111.1 |
| 21282271 | NP_645359.1 |
| 317130810 | YP_004097092.1 |
| 374397432 | EHQ68642.1 |
| 152977571 | YP_001377088.1 |
| 386830232 | YP_006236886.1 |
| 334276682 | EGL94935.1 |
| 385780852 | YP_005757023.1 |
| 82750292 | YP_416033.1 |
| 56965670 | YP_177404.1 |
| 358051694 | ZP_09145835.1 |
| 239636797 | ZP_04677799.1 |
| 330685907 | EGG97536.1 |
| 384546866 | YP_005736119.1 |
| 228994103 | ZP_04154003.1 |
| 401726885 | EJT00094.1 |
| 229000173 | ZP_04159742.1 |
| 379795059 | YP_005325057.1 |
| 311032064 | ZP_07710154.1 |
| 229087876 | ZP_04219988.1 |
| 70727404 | YP_254320.1 |
| 386715945 | YP_006182269.1 |
| 323489299 | ZP_08094531.1 |
| 299536034 | ZP_07049352.1 |
| 389816722 | ZP_10207674.1 |
| 126650921 | ZP_01723132.1 |
| 212640580 | YP_002317100.1 |
| 224475733 | YP_002633339.1 |
| 251798799 | YP_003013530.1 |
| 312112678 | YP_003990994.1 |
| 336237140 | YP_004589756.1 |
| 386728346 | YP_006194729.1 |
| 314937089 | ZP_07844436.1 |
| 228475108 | ZP_04059835.1 |
| 374823144 | EHR87147.1 |
| 393202157 | YP_006463999.1 |
| 163943070 | YP_001647954.1 |
| 401311354 | EJS16661.1 |
| 206970225 | ZP_03231178.1 |

TABLE 1-continued

| NCBI GI Accession Number | NCBI RefSeq Accession Number |
|---|---|
| 229020608 | ZP_04177344.1 |
| 392958928 | ZP_10324425.1 |
| 218906569 | YP_002454403.1 |
| 401135057 | EJQ42663.1 |
| 253575332 | ZP_04852670.1 |
| 229124893 | ZP_04254069.1 |
| 401648378 | EJS65974.1 |
| 229034026 | ZP_04188974.1 |
| 401174736 | EJQ81943.1 |
| 229153549 | ZP_04281727.1 |
| 229099815 | ZP_04230739.1 |
| 30023418 | NP_835049.1 |
| 228924134 | ZP_04087410.1 |
| 228903866 | ZP_04067981.1 |
| 228968520 | ZP_04129508.1 |
| 42784562 | NP_981809.1 |
| 228988615 | ZP_04148701.1 |
| 30265410 | NP_847787.1 |
| 75758554 | ZP_00738674.1 |
| 118480419 | YP_897570.1 |
| 401795731 | AFQ09590.1 |
| 340355774 | ZP_08678448.1 |
| 401193405 | EJR00411.1 |
| 374602821 | ZP_09675809.1 |
| 239828647 | YP_002951271.1 |
| 289551609 | YP_003472513.1 |
| 401241592 | EJR47979.1 |
| 401093093 | EJQ01212.1 |
| 354584844 | ZP_09003736.1 |
| 401252388 | EJR58649.1 |
| 229065036 | ZP_04200333.1 |
| 401138051 | EJQ45626.1 |
| 315649374 | ZP_07902463.1 |
| 401643508 | EJS61205.1 |
| 152112371 | A4ITP5.2 |
| 138896991 | YP_001127444.1 |
| 196040963 | ZP_03108260.1 |
| 401077984 | EJP86305.1 |
| 229014553 | ZP_04171669.1 |
| 222152077 | YP_002561237.1 |
| 261409225 | YP_003245466.1 |
| 329926866 | ZP_08281269.1 |
| 319891573 | YP_004148448.1 |
| 386320088 | YP_006016251.1 |
| 347751826 | YP_004859391.1 |
| 374710660 | ZP_09715094.1 |
| 52695600 | 1T0T |
| 319768491 | YP_004133992.1 |
| 56421951 | YP_149269.1 |
| 297531616 | YP_003672891.1 |
| 261420821 | YP_003254503.1 |
| 375010605 | YP_004984238.1 |
| 301056856 | YP_003795067.1 |
| 336115528 | YP_004570295.1 |
| 73663434 | YP_302215.1 |
| 297585491 | YP_003701271.1 |
| 365233554 | EHM74501.1 |
| 347549512 | YP_004855840.1 |
| 16801283 | NP_471551.1 |
| 255022443 | ZP_05294429.1 |
| 23100478 | NP_693945.1 |
| 217963726 | YP_002349404.1 |
| 46908349 | YP_014738.1 |
| 16804152 | NP_465637.1 |
| 290894126 | ZP_06557098.1 |
| 386732857 | YP_006206353.1 |
| 116873548 | YP_850329.1 |
| 399054122 | ZP_10742752.1 |
| 400171111 | ZP_10786628.1 |
| 365227200 | EHM68402.1 |
| 381184708 | ZP_09893243.1 |
| 315304220 | ZP_07874585.1 |
| 308070609 | YP_003872214.1 |
| 390455464 | ZP_10240992.1 |
| 375310122 | ZP_09775400.1 |
| 392971201 | ZP_10336597.1 |
| 289435463 | YP_003465335.1 |
| 310643795 | YP_003948553.1 |
| 398812996 | ZP_10571701.1 |
| 313632394 | EFR99424.1 |
| 350547382 | ZP_08916707.1 |
| 374320146 | YP_005073275.1 |
| 226314140 | YP_002774036.1 |
| 47570390 | ZP_00241031.1 |
| 297191327 | ZP_06908725.1 |
| 254818553 | ZP_05223554.1 |
| 379755414 | YP_005344086.1 |
| 334138528 | ZP_08511946.1 |
| 296171936 | ZP_06852981.1 |
| 371546895 | EHN75321.1 |
| 21224373 | NP_630152.1 |
| 357004127 | ZP_09069126.1 |
| 294632032 | ZP_06710592.1 |
| 302557663 | ZP_07310005.1 |
| 381210903 | ZP_09917974.1 |
| 392416039 | YP_006452644.1 |
| 400536789 | ZP_10800323.1 |
| 329940188 | ZP_08289470.1 |
| 29828763 | NP_823397.1 |
| 340627677 | YP_004746129.1 |
| 41408895 | NP_961731.1 |
| 291436567 | ZP_06575957.1 |
| 386843184 | YP_006248242.1 |
| 385995584 | YP_005913882.1 |
| 291454875 | ZP_06594265.1 |
| 289570850 | ZP_06451077.1 |
| 15609813 | NP_217192.1 |
| 289444218 | ZP_06433962.1 |
| 313607606 | EFR83886.1 |
| 299822310 | ZP_07054196.1 |
| 290956576 | YP_003487758.1 |
| 383823529 | ZP_09978719.1 |
| 240169729 | ZP_04748388.1 |
| 345021484 | ZP_08785097.1 |
| 54025706 | YP_119948.1 |
| 297203093 | ZP_06920490.1 |
| 304408214 | ZP_07389863.1 |
| 383638911 | ZP_09951317.1 |
| 357021607 | ZP_09083838.1 |
| 342306657 | BAK54746.1 |
| 15922480 | NP_378149.1 |
| 375142573 | YP_005003222.1 |
| 395771103 | ZP_10451618.1 |
| 389865542 | YP_006367783.1 |
| 357402256 | YP_004914181.1 |
| 294815684 | ZP_06774327.1 |
| 254393128 | ZP_05008286.1 |
| 374320324 | YP_005073453.1 |
| 118468878 | YP_887113.1 |
| 357410441 | YP_004922177.1 |
| 15790882 | NP_280706.1 |
| 383819186 | ZP_09974462.1 |
| 172056260 | YP_001812720.1 |
| 374608155 | ZP_09680954.1 |
| 13541622 | NP_111310.1 |
| 365861224 | ZP_09400999.1 |
| 302554904 | ZP_07307246.1 |
| 328885880 | CCA59119.1 |
| 269126008 | YP_003299378.1 |
| 345009959 | YP_004812313.1 |
| 345855716 | ZP_08808383.1 |
| 118618640 | YP_906972.1 |
| 284990411 | YP_003408965.1 |
| 295835898 | ZP_06822831.1 |
| 374985838 | YP_004961333.1 |
| 333919450 | YP_004493031.1 |
| 386382344 | ZP_10067963.1 |
| 372458364 | CCF13558.1 |
| 378814793 | ZP_09837647.1 |
| 302541889 | ZP_07294231.1 |
| 345002765 | YP_004805619.1 |
| 302537561 | ZP_07289903.1 |
| 378717676 | YP_005282565.1 |
| 239991583 | ZP_04712247.1 |

TABLE 1-continued

| NCBI GI Accession Number | NCBI RefSeq Accession Number |
|---|---|
| 326775901 | ZP_08235166.1 |
| 182435262 | YP_001822981.1 |
| 357392404 | YP_004907245.1 |
| 15898949 | NP_343554.1 |
| 291448583 | ZP_06587973.1 |
| 359767828 | ZP_09271610.1 |
| 398781574 | ZP_10545606.1 |
| 385777371 | YP_005649939.1 |
| 357009391 | ZP_09074390.1 |
| 262202198 | YP_003273406.1 |
| 379709823 | YP_005265028.1 |
| 339007351 | ZP_08639926.1 |
| 318061066 | ZP_07979787.1 |
| 271967974 | YP_003342170.1 |
| 259507404 | ZP_05750304.1 |
| 229586215 | YP_002844717.1 |
| 379736665 | YP_005330171.1 |
| 25028348 | NP_738402.1 |
| 309811739 | ZP_07705517.1 |
| 145224498 | YP_001135176.1 |
| 337747991 | YP_004642153.1 |
| 353184711 | EHB50235.1 |
| 15827508 | NP_301771.1 |
| 359772082 | ZP_09275520.1 |
| 315502680 | YP_004081567.1 |
| 302866123 | YP_003834760.1 |
| 111023818 | YP_706790.1 |
| 120403473 | YP_953302.1 |
| 375094985 | ZP_09741250.1 |
| 699157 | AAA62922.1 |
| 356666940 | EHI47011.1 |
| 229917171 | YP_002885817.1 |
| 335038759 | ZP_08531969.1 |
| 111027153 | YP_709131.1 |
| 108799181 | YP_639378.1 |
| 169826530 | YP_001696688.1 |
| 291301396 | YP_003512674.1 |
| 384100724 | ZP_10001781.1 |
| 377567646 | ZP_09796854.1 |
| 365870907 | ZP_09410448.1 |
| 388821964 | EIM44646.1 |
| 226366254 | YP_002784037.1 |
| 297561771 | YP_003680745.1 |
| 363420411 | ZP_09308503.1 |
| 384566547 | ZP_10013651.1 |
| 377561630 | ZP_09791073.1 |
| 119717893 | YP_924858.1 |
| 134098414 | YP_001104075.1 |
| 169630067 | YP_001703716.1 |
| 348171321 | ZP_08878215.1 |
| 377562766 | ZP_09792134.1 |
| 343924651 | ZP_08764195.1 |
| 15806494 | NP_295204.1 |
| 257056399 | YP_003134231.1 |
| 312139468 | YP_004006804.1 |
| 16081621 | NP_393983.1 |
| 331696710 | YP_004332949.1 |
| 319948480 | ZP_08022614.1 |
| 311742292 | ZP_07716101.1 |
| 296270232 | YP_003652864.1 |
| 317121335 | YP_004101338.1 |
| 354617379 | ZP_09034810.1 |
| 354610192 | ZP_09028148.1 |
| 359427086 | ZP_09218161.1 |
| 333991062 | YP_004523676.1 |
| 226306336 | YP_002766296.1 |
| 229491306 | ZP_04385132.1 |
| 256375690 | YP_003099350.1 |
| 145594081 | YP_001158378.1 |
| 111024859 | YP_707279.1 |
| 385674401 | ZP_10048329.1 |
| 386690160 | ZP_10088922.1 |
| 295695923 | YP_003589161.1 |
| 72162295 | YP_289952.1 |
| 330466519 | YP_004404262.1 |
| 378584109 | ZP_09832664.1 |
| 383831229 | ZP_09986318.1 |
| 296394322 | YP_003659206.1 |
| 238063535 | ZP_04608244.1 |
| 54654366 | AAV37056.1 |
| 313902589 | ZP_07835989.1 |
| 300781043 | ZP_07090897.1 |
| 317508457 | ZP_07966126.1 |
| 84496260 | ZP_00995114.1 |
| 302525787 | ZP_07278129.1 |
| 159037112 | YP_001536365.1 |
| 325002058 | ZP_08123170.1 |
| 376242999 | YP_005133851.1 |
| 375291064 | YP_005125604.1 |
| 227549138 | ZP_03979187.1 |
| 326384415 | ZP_08206095.1 |
| 383781997 | YP_005466564.1 |
| 256395904 | YP_003117468.1 |
| 376290601 | YP_005162848.1 |
| 38233979 | NP_939746.1 |
| 227504962 | ZP_03935011.1 |
| 387982647 | EIK56148.1 |
| 386852019 | YP_006270032.1 |
| 317125032 | YP_004099414.1 |
| 376248683 | YP_005140627.1 |
| 375101462 | ZP_09747725.1 |
| 375293270 | YP_005127809.1 |
| 296139503 | YP_003646846.1 |
| 152965553 | YP_001361337.1 |
| 359421112 | ZP_09213042.1 |
| 376293404 | YP_005165078.1 |
| 19553103 | NP_601105.1 |
| 145295803 | YP_001138624.1 |
| 334564734 | ZP_08517725.1 |
| 284031650 | YP_003381581.1 |
| 227503493 | ZP_03933542.1 |
| 377575250 | ZP_09804244.1 |
| 344044034 | EGV39715.1 |
| 306836259 | ZP_07469241.1 |
| 311739576 | ZP_07713411.1 |
| 255325114 | ZP_05366220.1 |
| 354511692 | EHE84598.1 |
| 296117770 | ZP_06836354.1 |
| 325283524 | YP_004256065.1 |
| 296130245 | YP_003637495.1 |
| 288917125 | ZP_06411495.1 |
| 226355654 | YP_002785394.1 |
| 336117965 | YP_004572733.1 |
| 326332270 | ZP_08198550.1 |
| 225021282 | ZP_03710474.1 |
| 237785637 | YP_002906342.1 |
| 357588794 | ZP_09127460.1 |
| 397729455 | ZP_10496235.1 |
| 111017350 | YP_700322.1 |
| 227833265 | YP_002834972.1 |
| 337290914 | YP_004629935.1 |
| 336320168 | YP_004600136.1 |
| 387138794 | YP_005694773.1 |
| 383314378 | YP_005375233.1 |
| 379715495 | YP_005303832.1 |
| 386740528 | YP_006213708.1 |
| 339628143 | YP_004719786.1 |
| 300858614 | YP_003783597.1 |
| 375288794 | YP_005123335.1 |
| 392400729 | YP_006437329.1 |
| 70605865 | YP_254735.1 |
| 386855711 | YP_006259888.1 |
| 300784551 | YP_003764842.1 |
| 86740042 | YP_480442.1 |
| 384515826 | YP_005710918.1 |
| 76801774 | YP_326782.1 |
| 356664861 | EHI44943.1 |
| 332798007 | YP_004459507.1 |
| 358445417 | ZP_09156027.1 |
| 260906569 | ZP_05914891.1 |
| 117928587 | YP_873138.1 |
| 167465230 | ZP_02330319.1 |
| 388821007 | EIM43781.1 |
| 334337905 | YP_004543057.1 |

TABLE 1-continued

| NCBI GI Accession Number | NCBI RefSeq Accession Number |
|---|---|
| 399577847 | ZP_10771599.1 |
| 256833104 | YP_003161831.1 |
| 332669795 | YP_004452803.1 |
| 312196140 | YP_004016201.1 |
| 385802483 | YP_005838883.1 |
| 295394782 | ZP_06804997.1 |
| 158316929 | YP_001509437.1 |
| 379057271 | ZP_09847797.1 |
| 340794530 | YP_004759993.1 |
| 336177818 | YP_004583193.1 |
| 110667069 | YP_656880.1 |
| 195927607 | 3DTZ |
| 94985810 | YP_605174.1 |
| 292656006 | YP_003535903.1 |
| 284041622 | YP_003391962.1 |
| 222480603 | YP_002566840.1 |
| 68536150 | YP_250855.1 |
| 358462858 | ZP_09172965.1 |
| 218289621 | ZP_03493841.1 |
| 302522536 | ZP_07274878.1 |
| 258511732 | YP_003185166.1 |
| 389847397 | YP_006349636.1 |
| 213964421 | ZP_03392621.1 |
| 313125252 | YP_004035516.1 |
| 227488766 | ZP_03919082.1 |
| 297627503 | YP_003689266.1 |
| 333373995 | ZP_08465888.1 |
| 48477890 | YP_023596.1 |
| 386359782 | YP_006058027.1 |
| 172039722 | YP_001799436.1 |
| 297567364 | YP_003686336.1 |
| 111221538 | YP_712332.1 |
| 269794165 | YP_003313620.1 |
| 229819585 | YP_002881111.1 |
| 269957406 | YP_003327195.1 |
| 116619486 | YP_821642.1 |
| 392943943 | ZP_10309585.1 |
| 146303506 | YP_001190822.1 |
| 46199654 | YP_005321.1 |
| 381191171 | ZP_09898682.1 |
| 291295788 | YP_003507186.1 |
| 300710235 | YP_003736049.1 |
| 55670428 | 1VDH |
| 401679226 | ZP_10811159.1 |
| 336326041 | YP_004606007.1 |
| 330835234 | YP_004409962.1 |
| 303230308 | ZP_07317073.1 |
| 384440419 | YP_005655143.1 |
| 303228654 | ZP_07315479.1 |
| 302038380 | YP_003798702.1 |
| 256825385 | YP_003149345.1 |
| 374632137 | ZP_09704511.1 |
| 284107237 | ZP_06386378.1 |
| 298252251 | ZP_06976054.1 |
| 367471078 | ZP_09470737.1 |
| 320449344 | YP_004201440.1 |
| 225872477 | YP_002753932.1 |
| 218296104 | ZP_03496873.1 |
| 269839067 | YP_003323759.1 |
| 342214592 | ZP_08707276.1 |
| 385652938 | ZP_10047491.1 |
| 383621121 | ZP_09947527.1 |
| 108803590 | YP_643527.1 |
| 257052298 | YP_003130131.1 |
| 257387306 | YP_003177079.1 |
| 148271773 | YP_001221334.1 |
| 383806533 | ZP_09962095.1 |
| 345005866 | YP_004808719.1 |
| 395236980 | ZP_10415106.1 |
| 340344386 | ZP_08667518.1 |
| 167043725 | ABZ08417.1 |
| 258651774 | YP_003200930.1 |
| 313893828 | ZP_07827394.1 |
| 344210645 | YP_004794965.1 |
| 386772469 | ZP_10094847.1 |
| 163839968 | YP_001624373.1 |
| 322368317 | ZP_08042886.1 |

TABLE 1-continued

| NCBI GI Accession Number | NCBI RefSeq Accession Number |
|---|---|
| 118430948 | NP_147071.2 |
| 386875231 | ZP_10117418.1 |
| 365906153 | ZP_09443912.1 |
| 384135398 | YP_005518112.1 |
| 161723231 | YP_137518.2 |
| 55232393 | AAV47812.1 |
| 352125886 | ZP_08969712.1 |
| 269928683 | YP_003321004.1 |
| 170783142 | YP_001711476.1 |
| 298526148 | ZP_07013557.1 |
| 380300719 | ZP_09850412.1 |
| 257069785 | YP_003156040.1 |
| 282849314 | ZP_06258699.1 |
| 294793131 | ZP_06758277.1 |
| 325963980 | YP_004241886.1 |
| 88854545 | ZP_01129212.1 |
| 257075934 | ZP_05570295.1 |
| 365850812 | ZP_09391271.1 |
| 221635966 | YP_002523842.1 |
| 359778406 | ZP_09281675.1 |
| 323358315 | YP_004224711.1 |
| 269797286 | YP_003311186.1 |
| 333976464 | EGL77331.1 |
| 294794831 | ZP_06759966.1 |
| 336254860 | YP_004597967.1 |
| 161528023 | YP_001581849.1 |
| 390958054 | YP_006421811.1 |
| 220913236 | YP_002488545.1 |
| 390565895 | ZP_10246467.1 |
| 116671315 | YP_832248.1 |
| 118576599 | YP_876342.1 |
| 238019896 | ZP_04600322.1 |
| 315283182 | ZP_07871432.1 |
| 119960759 | YP_948465.1 |
| 352114985 | ZP_08963219.1 |
| 329764724 | ZP_08256319.1 |
| 394761213 | EJF43622.1 |
| 393796958 | ZP_10380322.1 |
| 289581178 | YP_003479644.1 |
| 400976087 | ZP_10803318.1 |
| 300741889 | ZP_07071910.1 |
| 259502145 | ZP_05745047.1 |
| 393796863 | ZP_10380227.1 |
| 159900062 | YP_001546309.1 |
| 89100748 | ZP_01173602.1 |
| 311111782 | YP_003983004.1 |
| 255326984 | ZP_05368060.1 |
| 320106349 | YP_004181939.1 |
| 161486757 | YP_591030.2 |
| 283457694 | YP_003362280.1 |
| 94551032 | ABF40956.1 |
| 284166731 | YP_003405010.1 |
| 397774405 | YP_006541951.1 |
| 322435228 | YP_004217440.1 |
| 269217809 | ZP_06161663.1 |
| 227496736 | ZP_03927010.1 |
| 383810118 | ZP_09965625.1 |
| 395203147 | ZP_10394381.1 |
| 374312300 | YP_005058730.1 |
| 397670494 | YP_006512029.1 |
| 326772613 | ZP_08231897.1 |
| 313806438 | EFS44945.1 |
| 313793129 | EFS41196.1 |
| 313802783 | EFS44001.1 |
| 315082765 | EFT54741.1 |
| 327334886 | EGE76597.1 |
| 313810987 | EFS48701.1 |
| 313772848 | EFS38814.1 |
| 50841796 | YP_055023.1 |
| 379978901 | EIA12225.1 |
| 295129873 | YP_003580536.1 |
| 353343976 | EHB88289.1 |
| 315082092 | EFT54068.1 |
| 340774183 | EGR96670.1 |
| 350568884 | ZP_08937282.1 |
| 343522997 | ZP_08759962.1 |
| 340358532 | ZP_08681049.1 |

TABLE 1-continued

| NCBI GI Accession Number | NCBI RefSeq Accession Number |
|---|---|
| 308177933 | YP_003917339.1 |
| 313821947 | EFS59661.1 |
| 313765238 | EFS36602.1 |
| 313828705 | EFS66419.1 |
| 365973206 | YP_004954765.1 |
| 365962026 | YP_004943592.1 |
| 400293990 | ZP_10795815.1 |
| 319760122 | YP_004124061.1 |
| 327329287 | EGE71047.1 |
| 386070848 | YP_005985744.1 |
| 282853365 | ZP_06262702.1 |
| 320532492 | ZP_08033313.1 |
| 239918009 | YP_002957567.1 |
| 342212563 | ZP_08705288.1 |
| 365829316 | ZP_09371052.1 |
| 293189110 | ZP_06607836.1 |
| 329945534 | ZP_08293272.1 |
| 289705148 | ZP_06501552.1 |
| 325066698 | ZP_08125371.1 |
| 154509628 | ZP_02045270.1 |
| 399523435 | ZP_10764076.1 |
| 184200497 | YP_001854704.1 |
| 313814508 | EFS52222.1 |
| 396585876 | ZP_10486044.1 |
| 148655882 | YP_001276087.1 |
| 378551105 | ZP_09826321.1 |
| 365825602 | ZP_09367556.1 |
| 156742004 | YP_001432133.1 |
| 315604999 | ZP_07880053.1 |
| 399527499 | ZP_10767199.1 |
| 307635429 | ADN79128.1 |
| 46202510 | ZP_00208549.1 |
| 316983367 | 3Q08 |
| 224510506 | 2VXH |
| 168203364 | ACA21505.1 |
| 373252940 | ZP_09541058.1 |
| 381398954 | ZP_09924225.1 |
| 307635431 | ADN79129.1 |
| 349806848 | AEQ19297.1 |
| 196230396 | ZP_03129258.1 |
| 397737933 | ZP_10504580.1 |
| 389798300 | ZP_10201323.1 |
| 352090357 | ZP_08954468.1 |
| 389811160 | ZP_10206102.1 |
| 171911071 | ZP_02926541.1 |
| 255513657 | EET89922.1 |
| 28493701 | NP_787862.1 |
| 223935944 | ZP_03627859.1 |
| 373482185 | ZP_09572994.1 |
| 384915640 | ZP_10015852.1 |
| 269986639 | EEZ92920.1 |
| 335050425 | ZP_08543391.1 |
| 290558840 | EFD92232.1 |
| 290559836 | EFD93159.1 |
| 87311298 | ZP_01093420.1 |
| 301598730 | 3NN1 |
| 301598745 | 3NN4 |
| 301598740 | 3NN3 |
| 327542310 | EGF28797.1 |
| 302036741 | YP_003797063.1 |
| 149176472 | ZP_01855085.1 |
| 161579027 | NP_869234.2 |
| 189218926 | YP_001939567.1 |
| 255018722 | ZP_05290848.1 |
| 32446784 | CAD76620.1 |
| 296124023 | YP_003631801.1 |
| 283778293 | YP_003369048.1 |
| 227876575 | ZP_03994685.1 |
| 269977766 | ZP_06184726.1 |
| 315657647 | ZP_07910529.1 |
| 315654427 | ZP_07907335.1 |
| 298345852 | YP_003718539.1 |
| 256372606 | YP_003110430.1 |
| 262384993 | ACY64494.1 |
| 46948114 | AAT07039.1 |
| 262385037 | ACY64516.1 |
| 262384991 | ACY64493.1 |
| 262384971 | ACY64483.1 |
| 262385029 | ACY64512.1 |
| 262384973 | ACY64484.1 |
| 262385059 | ACY64527.1 |
| 262385013 | ACY64504.1 |
| 46948116 | AAT07040.1 |
| 46948118 | AAT07041.1 |
| 46948120 | AAT07042.1 |
| 363805181 | AEW31185.1 |
| 363805179 | AEW31184.1 |
| 78217052 | ABB36663.1 |
| 262385079 | ACY64537.1 |
| 363805183 | AEW31186.1 |
| 346987801 | AEO51751.1 |
| 78217078 | ABB36674.1 |
| 78217063 | ABB36667.1 |
| 78217076 | ABB36673.1 |
| 78217080 | ABB36675.1 |
| 78217071 | ABB36671.1 |
| 262384985 | ACY64490.1 |
| 262384943 | ACY64469.1 |
| 262384965 | ACY64480.1 |
| 262384995 | ACY64495.1 |
| 262384967 | ACY64481.1 |
| 262384969 | ACY64482.1 |
| 262385017 | ACY64506.1 |
| 262385031 | ACY64513.1 |
| 346987805 | AEO51753.1 |
| 262384981 | ACY64488.1 |
| 78217082 | ABB36676.1 |
| 262384945 | ACY64470.1 |
| 262385069 | ACY64532.1 |
| 262384975 | ACY64485.1 |
| 262384953 | ACY64474.1 |
| 262384947 | ACY64471.1 |
| 262385065 | ACY64530.1 |
| 262385057 | ACY64526.1 |
| 262384955 | ACY64475.1 |
| 262385011 | ACY64503.1 |
| 262384949 | ACY64472.1 |
| 262385083 | ACY64539.1 |
| 262385055 | ACY64525.1 |
| 262385073 | ACY64534.1 |
| 262384989 | ACY64492.1 |
| 262385023 | ACY64509.1 |
| 46948132 | AAT07048.1 |
| 78217067 | ABB36669.1 |
| 262385003 | ACY64499.1 |
| 78217050 | ABB36662.1 |
| 46948130 | AAT07047.1 |
| 262384977 | ACY64486.1 |
| 78217065 | ABB36668.1 |
| 262384951 | ACY64473.1 |
| 262384957 | ACY64476.1 |
| 262385049 | ACY64522.1 |
| 374346276 | BAL46758.1 |
| 262385071 | ACY64533.1 |
| 262385001 | ACY64498.1 |
| 78217056 | ABB36664.1 |
| 262385039 | ACY64517.1 |
| 78217048 | ABB36661.1 |
| 374346274 | BAL46757.1 |
| 374346222 | BAL46731.1 |
| 46948134 | AAT07049.1 |
| 374346234 | BAL46737.1 |
| 262384959 | ACY64477.1 |
| 374346224 | BAL46732.1 |
| 46948142 | AAT07053.1 |
| 78217058 | ABB36665.1 |
| 262385033 | ACY64514.1 |
| 374346254 | BAL46747.1 |
| 374346264 | BAL46752.1 |
| 262384979 | ACY64487.1 |
| 374346334 | BAL46787.1 |
| 374346252 | BAL46746.1 |
| 374346318 | BAL46779.1 |

TABLE 1-continued

| NCBI GI Accession Number | NCBI RefSeq Accession Number |
|---|---|
| 374346306 | BAL46773.1 |
| 374346280 | BAL46760.1 |
| 85815563 | CAI54237.1 |
| 374346330 | BAL46785.1 |
| 374346236 | BAL46738.1 |
| 374346194 | BAL46717.1 |
| 374346206 | BAL46723.1 |
| 374346196 | BAL46718.1 |
| 46948124 | AAT07044.1 |
| 374346268 | BAL46754.1 |
| 374346272 | BAL46756.1 |
| 374346292 | BAL46766.1 |
| 374346218 | BAL46729.1 |
| 374346198 | BAL46719.1 |
| 374346322 | BAL46781.1 |
| 78217069 | ABB36670.1 |
| 374346278 | BAL46759.1 |
| 374346298 | BAL46769.1 |
| 374346210 | BAL46725.1 |
| 374346214 | BAL46727.1 |
| 78217073 | ABB36672.1 |
| 374346202 | BAL46721.1 |
| 46948140 | AAT07052.1 |
| 346987803 | AEO51752.1 |
| 374346288 | BAL46764.1 |
| 46948138 | AAT07051.1 |
| 46948128 | AAT07046.1 |
| 374346204 | BAL46722.1 |
| 46948136 | AAT07050.1 |
| 374346244 | BAL46742.1 |
| 46948126 | AAT07045.1 |
| 374346332 | BAL46786.1 |
| 374346308 | BAL46774.1 |
| 254733624 | ZP_05191341.1 |
| 89101109 | ZP_01173946.1 |
| 374346226 | BAL46733.1 |
| 374346230 | BAL46735.1 |
| 124516141 | EAY57649.1 |
| 374346192 | BAL46716.1 |
| 294871860 | XP_002766074.1 |
| 294941712 | XP_002783202.1 |
| 206602939 | EDZ39419.1 |
| 294873397 | XP_002766607.1 |
| 294868340 | XP_002765489.1 |
| 399026596 | ZP_10728314.1 |
| 294868342 | XP_002765490.1 |
| 392966205 | ZP_10331624.1 |
| 46204585 | ZP_00049779.2 |
| 251770823 | EES51411.1 |
| 388565844 | ZP_10152326.1 |
| 152983035 | YP_001352597.1 |
| 54303991 | CAH04648.1 |
| 149925487 | ZP_01913751.1 |
| 385651069 | ZP_10045622.1 |
| 383767747 | YP_005446729.1 |
| 187928564 | YP_001899051.1 |
| 88810506 | ZP_01125763.1 |
| 162453252 | YP_001615619.1 |
| 294868338 | XP_002765488.1 |
| 85715952 | ZP_01046929.1 |
| 384215662 | YP_005606828.1 |
| 162453114 | YP_001615481.1 |
| 222831855 | EEE70332.1 |
| 37520735 | NP_924112.1 |
| 294873395 | XP_002766606.1 |
| 374346304 | BAL46772.1 |
| 319760141 | YP_004124080.1 |
| 383774186 | YP_005453253.1 |
| 399020141 | ZP_10722281.1 |
| 398822562 | ZP_10580941.1 |
| 283778666 | YP_003369421.1 |
| 290791109 | ADD63334.1 |
| 386398282 | ZP_10083060.1 |
| 383762862 | YP_005441844.1 |
| 146340409 | YP_001205457.1 |
| 75676626 | YP_319047.1 |
| 339717590 | 3QPI |
| 146283668 | YP_001173821.1 |
| 374577875 | ZP_09650971.1 |
| 172039718 | YP_001799432.1 |
| 338971876 | ZP_08627255.1 |
| 315283180 | ZP_07871431.1 |
| 330015852 | ZP_08308323.1 |
| 27382462 | NP_773991.1 |
| 393163430 | EJC63483.1 |

Chlorite Dismutase Homologs

In some embodiments, a chlorite dismutase polypeptide of the present disclosure is a homolog of any of the chlorite dismutase polypeptides listed in Table 1. In certain embodiments, a chlorite dismutase polypeptide of the present disclosure has an amino acid sequence that is at least 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of a polypeptide having the RefSeq accession number YP_005026408.1, YP_285781.1, AAM92878.1, WP_014235269.1, AAT07043.1, WP_009867516.1, CAC14884.1, WP_013516316.1, ACA21503.1, YP_004267835.1, EFH80711.1, YP_004178041.1, YP_004367213.1, YP_004058724.1, or YP_004172359.1 and has chlorite dismutase activity.

Homologs of the polypeptides described herein may also be used in the present disclosure. As used herein, "homology" refers to sequence similarity between a reference sequence and at least a fragment of a second sequence. Homologs may be identified by any method known in the art, preferably, by using the BLAST tool to compare a reference sequence to a single second sequence or fragment of a sequence or to a database of sequences. As described below, BLAST will compare sequences based upon percent identity and similarity.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 29% identity, optionally 25%, 30%, 40%, 45%, 50%, 55%, 60%, 65%, 70%, 75%, 80%, 85%, 90%, 95%, 99% or 100% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200, or more amino acids) in length.

Methods of alignment of sequences for comparison are well-known in the art. For example, the determination of percent sequence identity between any two sequences can be accomplished using a mathematical algorithm. Non-limiting examples of such mathematical algorithms are the algorithm of Myers and Miller (1988) CABIOS 4:11 17; the local homology algorithm of Smith and Waterman (1981) J. Mol. Biol. 147:195-7; the homology alignment algorithm of Needleman and Wunsch (1970) J. Mol. Biol. 48:443 453; the search-for-similarity-method of Pearson and Lipman (1988)

Proc. Natl. Acad. Sci. 85:2444 2448; the algorithm of Karlin and Altschul (1990) Proc. Natl. Acad. Sci. USA 872264, modified as in Karlin and Altschul (1993) Proc. Natl. Acad. Sci. USA 90:5873 5877.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window," as used herein, includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1981), by the homology alignment algorithm of Needleman and Wunsch (1970) *J Mol Biol* 48(3):443-453, by the search for similarity method of Pearson and Lipman (1988) *Proc Natl Acad Sci USA* 85(8):2444-2448, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection [see, e.g., Brent et al., (2003) Current Protocols in Molecular Biology, John Wiley & Sons, Inc. (Ringbou Ed)].

To determine the sequence identity between a reference sequence and a query sequence (e.g., in determining the sequence identity between a chlorite dismutase polypeptide of the present disclosure and another polypeptide), a dynamic programming algorithm may be used to find the optimal alignment between the sequences. Optimal alignments may be found for both global sequence alignments and local sequence alignments. Many examples of suitable dynamic programming algorithms for finding optimal alignments are known in the art. These may include, without limitation, Needleman-Wunsch (Needleman and Wunsch (1970) J. Mol. Biol. 48:443-453) and Smith-Waterman (Smith and Waterman (1981) J. Mol. Biol. 147:195-7).

Two examples of other algorithms that may be used for determining percent sequence identity and sequence similarity are the BLAST and BLAST 2.0 algorithms, which are described in Altschul et al. (1997) Nucleic Acids Res 25(17): 3389-3402 and Altschul et al. (1990) J. Mol Biol 215(3)-403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4, and a comparison of both strands. For amino acid sequences, the BLASTP program uses as defaults a wordlength of 3, and expectation (E) of 10, and the BLOSUM62 scoring matrix [see Henikoff and Henikoff, (1992) Proc Natl Acad Sci USA 89(22): 10915-10919] alignments (B) of 50, expectation (E) of 10, M=5, N=−4, and a comparison of both strands.

The BLAST algorithm also performs a statistical analysis of the similarity between two sequences (see, e.g., Karlin and Altschul, (1993) Proc Natl Acad Sci USA 90(12):5873-5877). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Other than percentage of sequence identity noted above, another indication that two nucleic acid sequences or polypeptides are substantially identical is that the polypeptide encoded by the first nucleic acid is immunologically cross-reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions. Yet another indication that two nucleic acid sequences are substantially identical is that the same primers can be used to amplify the sequence.

Microorganisms

Recombinantly Engineered Host Microorganisms

Certain aspects of the present disclosure relate to culturing a cell that is recombinantly engineered. As used herein, the terms "host," "host microorganism," "host cell," and "cell" are used interchangeably and refer to a cell of the present disclosure that is recombinantly engineered.

Any prokaryotic or eukaryotic cell may be used in the present disclosure so long as it remains viable after being recombinantly engineered (e.g., by being transformed with a sequence of nucleic acids). Preferably, the cell is not adversely affected by the transduction of the necessary nucleic acid sequences, the subsequent expression of the proteins or the resulting intermediates. In some embodiments, the recombinantly engineered cell is a bacterial, yeast, or fungal cell. The term "bacteria" refers to microorganisms within the domain of bacteria. Phyla within the domain or kingdom of bacteria include Acidobacteria, Actinobacteria, Aquificae, Armatimonadetes, Bacteroidetes, Caldiserica, Chlamydiae, Chlorobi, Chloroflexi, Chrysiogenetes, Cyanobacteria, Deferribacteres, Deinococcusthermus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia. The term "fungal cells" refers to eukaryotic organisms within the kingdom of fungi. Phyla within the kingdom of fungi include Ascomycota, Basidiomycota, Blastocladiomycota, Chytridiomycota, Glomeromycota, Microsporidia, and Neocallimastigomycota. As used herein, the term "yeast" refers to any fungal cell within the phyla Ascomycota and Basidiomycota. Without being limited to these organisms, many types of yeast used in laboratory and commercial settings are part of the phylum Ascomycota.

In some embodiments, a cultured cell is used to generate a fermentation product. In certain embodiments, the cell is a bacterial, yeast, or fungal cell. Exemplary bacterial, yeast, or fungal cells include without limitation the following species: *Saccharomyces* sp., *Saccharomyces cerevisiae*, *Saccharomyces monacensis*, *Saccharomyces bayanus*, *Saccharomyces pastorianus*, *Saccharomyces carlsbergensis*, *Saccharomyces pombe*, *Trichoderma reesei*, *Neurospora crassa*, *Neurospora* sp., *Kluyveromyces* sp., *Kluyveromyces marxiamus*, *Kluyveromyces lactis*, *Kluyveromyces fragilis*, *Pichia stipitis*, *Pichia pastoris*, *Pichia* sp., *Sporotrichum thermophile*, *Candida shehatae*, *Candida tropicalis*, *Neurospora crassa*, *Zymomonas mobilis*, *Clostridium* sp., *Clostridium saccharoperbutylacetonicum*, *Clostridium phytofermentans*, *Clostridium thermocellum*, *Clostridium beijerinckii*, *Clostridium acetobutylicum*, *Clostridium botulinum*, *Clostridium butyricum*, *Clostridium diolis*, *Clostridium ljungdahlii*, *Clostridium aerotolerans*, *Clostridium cellulolyticum*, *Clostridium tyrobutyricum*, *Clostridium pasteurianum*, *Moorella thermoacetica*, *Escherichia coli*, *Klebsiella oxytoca*, *Thermoanaerobacterium saccharolyticum*, *Yarrowia lipolytica*, *Yarrowia* sp., *Bacillus subtilis*, and *Bacillus* sp.

In some embodiments, the cell is a *Clostridium* cell. As used herein, "*Clostridium*" may include any species of bacterium from the genus *Clostridium*. This genus encompasses a group of over 100 bacterial species that are Gram-positive and form a subset of the Firmicutes phylum of prokaryotes.

In some embodiments, the bacterial, yeast, or fungal cell does not endogenously express a chlorite dismutase. In other embodiments, the bacterial, yeast, or fungal cell may endogenously express a chlorite dismutase.

In some embodiments, the recombinantly engineered cell is an animal cell. In some embodiments, the recombinantly engineered animal cell is a mammalian or insect cell. Examples of mammalian cells may include without limitation a human cell (e.g., a human embryonic kidney cell line such as a 293 cell, a cancer cell line such as a HeLa cell, a hybridoma, or any other human cell line), a non-human primate cell (e.g., a monkey kidney cell such as a CV 1 cell or an African green monkey kidney cell such as a VERO cell), a mouse cell (e.g., a TM4 mouse sertoli cell, hybridoma, myeloma, or other mouse cell line), a hamster cell [e.g., a Chinese hamster ovary (CHO) or baby hamster kidney cell (BHK)], a dog cell, a cat cell, a rat cell, a farm animal cell, a horse cell, a donkey cell, a cow cell, and so forth. Examples of insect cells may include without limitation a *Spodopterafrugiperda* (e.g., an Sf9 cell) and a *Drosophila* cell (e.g., an S2 cell). In some embodiments, the recombinantly engineered cell is a plant cell (e.g., an algal cell or a transgenic plant cell). In some embodiments, the mammalian or insect cell is a cancer cell. In some embodiments, the vertebrate, invertebrate, or plant cell is used to generate a product, such as a polypeptide (e.g., an antibody or a recombinantly produced polypeptide).

Recombinant Engineering

Certain aspects of the present disclosure relate to a cell recombinantly engineered to express a chlorite dismutase polypeptide.

"Recombinant nucleic acid" or "heterologous nucleic acid" or "recombinant polynucleotide" as used herein refers to a polymer of nucleic acids where at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids contains two or more subsequences that are not found in the same relationship to each other in nature. For example, regarding instance (c), a recombinant nucleic acid sequence will have two or more sequences from unrelated genes arranged to make a new functional nucleic acid. Specifically, the present disclosure describes the introduction of an expression vector into a host cell, where the expression vector contains a nucleic acid sequence coding for a protein that is not normally found in a host cell or contains a nucleic acid coding for a protein that is normally found in a cell but is under the control of different regulatory sequences. With reference to the host cell's genome, then, the nucleic acid sequence that codes for the protein is recombinant. A polypeptide that is referred to as recombinant generally implies that it is encoded by a recombinant nucleic acid sequence in the host cell.

A "recombinant" polypeptide, protein, or enzyme of the present disclosure, is a polypeptide, protein, or enzyme that is encoded by a "recombinant nucleic acid" or "heterologous nucleic acid" or "recombinant polynucleotide."

In some embodiments, the nucleic acids encoding the desired polypeptides in the host cell may be heterologous to the host cell or these nucleic acids may be endogenous to the host cell but are operatively linked to heterologous promoters and/or control regions which result in the higher expression of the nucleic acid(s) in the host cell. In certain embodiments, the host cell does not naturally produce the desired polypeptides, and contains heterologous nucleic acid constructs capable of expressing one or more genes necessary for producing those molecules.

"Recombinantly engineered," "recombinantly modified," "genetically engineered," or "genetically modified" refers to any recombinant DNA or RNA method used to create a host cell that expresses either a heterologous or endogenous polypeptide at elevated levels, at lowered levels, or in a mutated form. In other words, the cell has been transfected, transformed, or transduced with a recombinant polynucleotide molecule, and thereby been altered so as to cause the cell to alter expression of a desired protein. Methods and vectors for recombinantly engineering host cells are well known in the art; for example various techniques are illustrated in Current Protocols in Molecular Biology, Ausubel et al., eds. (Wiley & Sons, New York, 1988, and quarterly updates). Recombinant engineering techniques include, without limitation, expression vectors, and targeted homologous recombination and gene activation (see, for example, U.S. Pat. No. 5,272,071).

In certain embodiments, recombinant engineering may include the expression of a single gene (e.g., a gene encoding a chlorite dismutase polypeptide), or it may include the expression of multiple genes encoding polypeptides, such as enzymes, of a biochemical pathway (e.g., biochemical production of a commodity chemical).

In some embodiments, the host cell is recombinantly engineered to express a chlorite dismutase. In some embodiments, the host cell is further recombinantly engineered to express one or more proteins for the production of a fermentation product. The nucleic acid(s) encoding the chlorite dismutase and other recombinant polypeptide(s) may be exogenous to the host cell, or these nucleic acids may be endogenous to the host cell but operatively linked to heterologous promoters and/or control regions which result in higher or differentially regulated expression in a host cell. Any recombinant nucleic acids may be used in combination with any other nucleic acid that encodes a protein which aids in or enables the desired expression, stability, subcellular localization, or activity of a chlorite dismutase polypeptide or one or more proteins for the production of a fermentation product.

In some embodiments, the host cell does not endogenously express a chlorite dismutase. "Endogenous" as used herein with reference to a particular cell refers to a polynucleotide or a polypeptide that is naturally found in the cell, e.g., a gene that was present in the cell when the cell was originally isolated from nature. "Exogenous" (used interchangeably with "heterologous") as used herein with reference to a polynucleotide or a polypeptide and a particular cell refers to a polynucleotide or a polypeptide not found in that particular species of cell in nature, but instead that is encoded by one or more recombinant polynucleotides.

In some embodiments, the host cell further contains one or more proteins necessary for heme biosynthesis. In some embodiments, a host cell of the present disclosure may endogenously express one or more proteins necessary for heme biosynthesis. In some embodiments, the host cell is further recombinantly engineered to express one or more proteins necessary for heme biosynthesis. Without wishing to be bound by theory, it is thought that heterologous expression of one or more proteins necessary for heme biosynthesis may be advantageous for chlorite dismutase activity, since the active site of a chlorite dismutase contains a heme group. A protein necessary for heme biosynthesis may refer to any protein whose presence and/or activity is required for and/or promotes one or more steps of heme biosynthesis (e.g., one or more steps in a heme biosynthesis pathway) in a host cell. For example, in some embodiments, a heme biosynthesis pathway may include one or more of the chemical reactions depicted in FIG. 11 of the present disclosure. Heterologous expression of one or more proteins necessary for heme biosynthesis may refer to expression of the one or more proteins in a host cell that does not endogenously express them, or it may refer to expression of the one or more proteins at a different level or otherwise regulated in a different manner in a host cell that also has endogenous expression of the one or more proteins.

Many proteins necessary for heme biosynthesis are known in the art (for more detailed description, see, e.g., Heinemann, I. U., et al. (2008) *Arch. Biochem. Biophys.* 474(2):238-51). In some embodiments, the one or more proteins necessary for heme biosynthesis are selected from uroporphyrinogen III decarboxylase, coproporphyrinogen III oxidase, protoporphyrinogen IX oxidase, and ferrochelatase.

Uroporphyrinogen III decarboxylase as used herein may refer to any protein that catalyzes the conversion of uroporphyrinogen III to coproporphyrinogen III and carbon dioxide. The EC classification for uroporphyrinogen III decarboxylase is EC 4.1.1.37. In the present disclosure, any enzyme demonstrated or predicted to have the activity corresponding to EC classification 4.1.1.37 is considered to be a uroporphyrinogen III decarboxylase polypeptide. The GO term ID for uroporphyrinogen III decarboxylase is GO: 0004853. In the present disclosure, any protein demonstrated or predicted to have the cellular component, biological process, or molecular function corresponding to the GO term ID GO: 0004853 is considered to be a uroporphyrinogen III decarboxylase polypeptide. A non-limiting example of a uroporphyrinogen III decarboxylase polypeptide described in the literature is HemE (see Nishimura, K. et al. (1993) *Gene* 133(1):109-13 for further description). Uroporphyrinogen III decarboxylase polypeptides from a variety of host organisms may be used, including without limitation *E. coli* (e.g., as described by NCBI Reference Sequence NP_418425), *B. subtilis* (e.g., as described by NCBI Reference Sequence NP_388893), *L monocytogenes* (e.g., as described by NCBI Reference Sequence CAD00290), *S. epidermidis* (e.g., as described by NCBI Reference Sequence AIR82849), and *S. mutans* (e.g., as described by NCBI Reference Sequence WP_024786000).

Coproporphyrinogen III oxidase (CPO) as used herein may refer to any protein that catalyzes the conversion of coproporphyrinogen III to protoporphyrinogen-IX and carbon dioxide. This reaction may be catalyzed by a CPO enzyme in an oxygen-dependent reaction that uses $O_2$ and H(+) as substrates. Alternatively, the reaction may also be catalyzed by a CPO enzyme in an oxygen-independent reaction that uses NADPH and S-adenosyl-L-methionine (SAM) as substrates. The EC classification for coproporphyrinogen III oxidase is EC 1.3.3.3. In the present disclosure, any enzyme demonstrated or predicted to have the activity corresponding to EC classification 1.3.3.3 is considered to be a coproporphyrinogen III oxidase polypeptide. The GO term ID for coproporphyrinogen III oxidase is GO: 0004109. In the present disclosure, any protein demonstrated or predicted to have the cellular component, biological process, or molecular function corresponding to the GO term ID GO: 0004109 is considered to be a coproporphyrinogen III oxidase polypeptide. A non-limiting example of an oxygen-independent coproporphyrinogen III oxidase polypeptide described in the literature is HemN, and a non-limiting example of an oxygen-dependent coproporphyrinogen III oxidase polypeptide described in the literature is HemF (see Layer, G. et al. (1993) *Biol. Chem.* 386(10):971-80 for further description). Coproporphyrinogen III oxidase polypeptides from a variety of host organisms may be used, including without limitation *E. coli* (e.g., as described by NCBI Reference Sequence NP_416931), *B. subtilis* (e.g., as described by NCBI Reference Sequence YP_007534533), *L monocytogenes* (e.g., as described by NCBI Reference Sequence CAC99554), *S. epidermidis* (e.g., as described by NCBI Reference Sequence NP_764825), and *S. mutans* (e.g., as described by NCBI Reference Sequence NP_721776).

Protoporphyrinogen IX oxidase as used herein may refer to any protein that catalyzes the conversion of protoporphyrinogen-IX to protoporphyrin-IX. This reaction may be catazlyed by a protoporphyrinogen IX oxidase in an oxygen-dependent or oxygen-independent mechanism. The EC classification for protoporphyrinogen IX oxidase is EC 1.3.3.4. In the present disclosure, any enzyme demonstrated or predicted to have the activity corresponding to EC classification 1.3.3.4 is considered to be a protoporphyrinogen IX oxidase polypeptide. The GO term ID for protoporphyrinogen IX oxidase is GO: 0070818. In the present disclosure, any protein demonstrated or predicted to have the cellular component, biological process, or molecular function corresponding to the GO term ID GO: GO: 0070818 is considered to be a protoporphyrinogen IX oxidase polypeptide. A non-limiting example of an oxygen-independent protoporphyrinogen IX oxidase polypeptide described in the literature is HemG (see Boynton, T. O. et al. (2009) *Biochemistry* 48(29):6705-11 for further description), and a non-limiting example of an oxygen-dependent protoporphyrinogen IX oxidase polypeptide is HemY (see Boynton, T. O. et al. (2011) *Appl. Environ. Microbiol.* 77(14):4795-801 for further description). Protoporphyrinogen IX oxidase polypeptides from a variety of host organisms may be used, including without limitation *E. coli* (e.g., as described by NCBI Reference Sequence NP_418292), *K. pneumoniae* (e.g., as described by NCBI Reference Sequence CED77855), and *V. parahaemolyticus* (e.g., as described by NCBI Reference Sequence NP_796412).

Ferrochelatase as used herein may refer to any protein that catalyzes the interconversion of protoporphyrin and protoheme. The EC classification for ferrochelatase is EC 4.99.1.1. In the present disclosure, any enzyme demonstrated or predicted to have the activity corresponding to EC classification 4.99.1.1 is considered to be a ferrochelatase polypeptide. The GO term ID for ferrochelatase is GO: 0004325. In the present disclosure, any protein demonstrated or predicted to have the cellular component, biological process, or molecular function corresponding to the GO term ID GO: GO: 0004325 is considered to be a ferrochelatase polypeptide. A non-limiting example of a ferrochelatase polypeptide described in the literature is HemH (see Frustaci, J. M. and O'Brian, M. R. (1993) *Appl. Environ. Microbiol.* 59(8):2347-51 for further description). Ferrochelatase polypeptides from a variety of host organisms may be used, including without limitation *E. coli* (e.g., as described by NCBI Reference Sequence NP_415008), *B. subtilis* (e.g., as described by NCBI Reference Sequence NP_388894), *L monocytogenes* (e.g., as described by NCBI Reference Sequence NP_465735), *S. epidermidis* (e.g., as described by NCBI Reference Sequence AIR83582), *S. mutans* (e.g., as described by NCBI Reference Sequence WP_024781571), and *K. pneumoniae* (e.g., as described by NCBI Reference Sequence YP_005225503).

In some embodiments, chlorite dismutase is expressed under the control of a promoter. "Under the control" refers to a recombinant nucleic acid that is operably linked to a control sequence, or promoter. The term "operably linked" as used herein refers to a configuration in which a control sequence or promoter is placed at an appropriate position relative to the coding sequence of the nucleic acid sequence such that the control sequence or promoter directs the expression of a polypeptide.

"Promoter" is used herein to refer to any nucleic acid sequence that regulates the initiation of transcription for a particular polypeptide-encoding nucleic acid under its control. A promoter does not typically include nucleic acids that are transcribed, but it rather serves to coordinate the assembly of components that initiate the transcription of other nucleic acid sequences under its control. A promoter may further serve to limit this assembly and subsequent transcription to specific prerequisite conditions. Prerequisite conditions may include expression in response to one or more environmental, temporal, or developmental cues; these cues may be from outside stimuli or internal functions of the cell. Bacterial and fungal cells possess a multitude of proteins that sense external or internal conditions and initiate signaling cascades ending in the binding of proteins to specific promoters and subsequent initiation of transcription of nucleic acid(s) under the control of the promoters. When transcription of a nucleic acid(s) is actively occurring downstream of a promoter, the promoter can be said to "drive" expression of the nucleic acid(s). A promoter minimally includes the genetic elements necessary for the initiation of transcription, and may further include one or more genetic elements that serve to specify the prerequisite conditions for transcriptional initiation. A promoter may be encoded by the endogenous genome of a host cell, or it may be introduced as part of a recombinantly engineered polynucleotide. A promoter sequence may be taken from one host species and used to drive expression of a gene in a host cell of a different species. A promoter sequence may also be artificially designed for a particular mode of expression in a particular species, through random mutation or rational design. In recombinant engineering applications, specific promoters are used to express a recombinant gene under a desired set of physiological or temporal conditions or to modulate the amount of expression of a recombinant nucleic acid.

In some embodiments, chlorite dismutase is expressed under the control of a constitutive promoter. A constitutive promoter is defined herein as a promoter that drives the expression of nucleic acid(s) continuously and without interruption in response to internal or external cues. Constitutive promoters are commonly used in recombinant engineering to ensure continuous expression of desired recombinant nucleic acid(s). Constitutive promoters often result in a robust amount of nucleic acid expression, and, as such, are used in many recombinant engineering applications to achieve a high level of recombinant protein and enzymatic activity. These promoters are therefore suited for applications wherein a product derived from an enzymatic activity is purified, for example the production of a hydrocarbon or hydrocarbon derivative by one or more recombinant proteins.

Many constitutive promoters are known and characterized in the art. Exemplary bacterial constitutive promoters include without limitation the *E. coli* promoters $P_{spc}$, $P_{bla}$, $PRNA_I$, $P_{RNAII}$, P1 and P2 from rrnB, and the lambda phage promoter $P_L$ (Liang, S. T. et al. (1999). J Mol Biol 292(1): 19-37). Exemplary yeast constitutive promoters include without limitation the ADH1, GPD, TEF1, TEF2, and HX77 promoters from *S. cerevisiae* (see, e.g., Sun, J. et al. (2012). Biotechnol Bioeng 109(8): 2082-92). Constitutive promoters functional in a wide variety of host bacterial and yeast cells are well known in the art.

In some embodiments, chlorite dismutase is expressed under the control of an inducible promoter. An inducible promoter is defined herein as a promoter that drives the expression of nucleic acid(s) selectively and reliably in response to a specific stimulus. An ideal inducible promoter will drive no nucleic acid expression in the absence of its specific stimulus but drive robust nucleic acid expression rapidly upon exposure to its specific stimulus. Additionally, some inducible promoters induce a graded level of expression that is tightly correlated with the amount of stimulus received. Stimuli for known inducible promoters include, for example, heat shock, exogenous compounds (e.g., a sugar, metal, drug, or phosphate), salts or osmotic shock, oxygen, and biological stimuli (e.g., a growth factor or pheromone).

Inducible promoters are often used in recombinant engineering applications to limit the expression of recombinant nucleic acid(s) to desired circumstances. For example, since high levels of recombinant protein expression may sometimes slow the growth of a host cell, the host cell may be grown in the absence of recombinant nucleic acid expression, and then the promoter may be induced when the host cells have reached a desired density. Many inducible promoters are known and characterized in the art. Exemplary bacterial inducible promoters include without limitation the E. coli promoters $P_{lac}$, $P_{trp}$, $P_{tac}$, $P_{T7}$, $P_{BAD}$, and $P_{lacUV5}$ (Nocadello, S. and Swennen, E. F. (2012). Microb Cell Fact 11:3). Exemplary yeast inducible promoters include without limitation the GAL1, GAL10, PHO5, PGK, and MFα1 promoters from S. cerevisiae (Romanos, M. A. et al. (1992). Yeast 8:423-88). Inducible promoters functional in a wide variety of host bacterial and yeast cells are well known in the art.

In some embodiments, chlorite dismutase is expressed under the control of a yeast promoter. In addition to those listed above, examples of suitable yeast promoters include without limitation pTDH3, pTEF1, pRPL18, pRNR2, and pREV1. In some embodiments, chlorite dismutase is expressed by operably linking a chlorite dismutase coding sequence with a terminator sequence (e.g., the S. cerevisiae ADH1 terminator). In some embodiments, chlorite dismutase is expressed in yeast from a centromere-based plasmid. A centromere-based plasmid may include any plasmid bearing a functional centromere sequence (e.g., the S. cerevisiae CEN6 sequence), which helps maintain the plasmid during cell division of the host cell. A yeast promoter of the present disclosure may refer to any promoter sequence that regulates the expression of a gene in any yeast of the present disclosure, including without limitation S. cerevisiae, Saccharomyces sp., Pichia pastoris, Pichia sp., Yarrowia lipolytica, Yarrowia sp., and any of the other yeasts described herein.

A recombinant polypeptide-encoding nucleic acid or plurality of polypeptide-encoding nucleic acids may be encoded by an expression vector. An expression vector contains one or more polypeptide-encoding nucleic acids, and it may further contain any desired elements that control the expression of the nucleic acid(s), as well as any elements that enable the replication and maintenance of the expression vector inside a given host cell. In some embodiments, one or more recombinant nucleic acids may be contained by the microorganism (e.g., a chlorite dismutase polypeptide and one or more proteins for the production of a fermentation product). All of the recombinant nucleic acids may be present on a single expression vector, or they may be encoded by multiple expression vectors. As such, they may be controlled together by the same genetic elements or controlled separately by distinct genetic elements. Furthermore, the recombinant nucleic acid(s) may be maintained separately from the host genome, or the recombinant nucleic acid(s) may be integrated into the host genome. In addition, recombinant nucleic acid(s) may be introduced without an expression vector. For example, nucleic acids may be directly introduced into a bacterial or fungal host cell's genome by homologous recombination or recombineering. When more than one recombinant nucleic acid is present, they may all be maintained separately from the host genome, or they may all be integrated into the host genome, or they may exist in any combination of separate and integrated.

Methods to produce recombinant microorganisms by introducing recombinant nucleic acids/proteins, and vectors suitable for this purpose, are well known in the art. For example, various techniques are illustrated in Current Protocols in Molecular Biology, Ausubel et al., eds. (Wiley & Sons, New York, 1988, and quarterly updates). Methods for transferring expression vectors into host cells are well known in the art. Specific methods and vectors may differ depending upon the species of the desired host cell. For example, bacterial host cells may be transformed by heat shock, calcium chloride treatment, electroporation, liposomes, or phage infection. Yeast host cells may be transformed by lithium acetate treatment (may further include carrier DNA and PEG treatment) or electroporation. These methods are included for illustrative purposes and are in no way intended to be limiting or comprehensive. Routine experimentation through means well known in the art may be used to determine whether a particular expression vector or transformation method is suited for a given host cell. Furthermore, reagents and vectors suitable for many different host microorganisms are commercially available and/or well known in the art.

Cell Culture

Certain aspects of the present disclosure relate to methods of culturing a cell. As defined herein, "culturing" a cell refers to introducing an appropriate culture medium, under appropriate conditions, to promote the growth of a cell. Methods of culturing various types of cells are known in the art. Culturing may be performed using a liquid or solid growth medium. Culturing may be performed under aerobic or anaerobic conditions where aerobic, anoxic, or anaerobic conditions are preferred based on the requirements of the microorganism and desired metabolic state of the microorganism. In addition to oxygen levels, other important conditions may include, without limitation, temperature, pressure, light, pH, and cell density.

In some embodiments, a culture medium is provided. A "culture medium" or "growth medium" as used herein refers to a mixture of components that supports the growth of cells. In some embodiments, the culture medium may exist in a liquid or solid phase. A culture medium of the present disclosure can contain any nutrients required for growth of microorganisms. In certain embodiments, the culture medium may further include any compound used to reduce the growth rate of, kill, or otherwise inhibit additional contaminating microorganisms. In some embodiments, the compound is chlorite. In certain embodiments, the growth medium is treated with chlorite in an amount sufficient to reduce the growth rate, kill, or otherwise inhibit additional contaminating microorganisms. The growth medium may also contain any compound used to modulate the expression of a nucleic acid, such as one operably linked to an inducible promoter (for example, when using a yeast cell, galactose may be added into the growth medium to activate expression of a recombinant nucleic acid operably linked to a GAL1 or GAL10 promoter). In further embodiments, the culture medium may lack specific nutrients or components to limit the growth of contaminants, select for microorganisms with a particular auxotrophic marker, or induce or repress expression of a nucleic acid responsive to levels of a particular component.

In some embodiments, the methods of the present disclosure may include culturing a host cell under conditions sufficient for the production of a fermentation product. In certain embodiments, culturing a host cell under conditions sufficient for the production of a fermentation product entails culturing the cells in a suitable culture medium.

Suitable culture media may differ among different microorganisms depending upon the biology of each microorganism. Selection of a culture medium, as well as selection of other parameters required for growth (e.g., temperature, oxygen levels, pressure, etc.), suitable for a given microorganism based on the biology of the microorganism are well known in the art. Examples of suitable culture media may include, without limitation, common commercially prepared media, such as Luria Bertani (LB) broth, Sabouraud Dextrose (SD) broth, or Yeast medium (YM) broth. In other embodiments, alternative defined or synthetic culture media may also be used.

In some embodiments, a host cell of the present disclosure that is recombinantly engineered to express a chlorite dismutase polypeptide is cultured under conditions where a chlorite dismutase polypeptide is expressed in the cell. As disclosed herein, conditions suitable for chlorite dismutase expression may refer, without limitation, to the nutrient composition, pH, temperature, oxygen level, and/or light exposure of the culture medium containing the host cell. In some embodiments, the conditions may allow for the chlorite dismutase polypeptide to be properly translated, processed, localized within the cell, and sufficiently stable and enzymatically active.

In some embodiments, a host cell of the present disclosure is cultured under micro-aerobic conditions. As used herein, "micro-aerobic conditions" may refer to any conditions for cell culture wherein the amount of oxygen is less than about 20% (the approximate amount of oxygen in the atmosphere). In some embodiments, the host cell is cultured in less than about 20% oxygen, less than about 19% oxygen, less than about 18% oxygen, less than about 17% oxygen, less than about 16% oxygen, less than about 15% oxygen, less than about 14% oxygen, less than about 13% oxygen, less than about 12% oxygen, less than about 11% oxygen, less than about 10% oxygen, less than about 9% oxygen, less than about 8% oxygen, less than about 7% oxygen, less than about 6% oxygen, less than about 5% oxygen, less than about 4% oxygen, less than about 3% oxygen, less than about 2% oxygen, or less than about 1% oxygen. Decreasing the amount of available oxygen is known to result in cellular stress. Without wishing to be bound to theory, it is thought that the presence of oxygen may aid cells cultured under such stress in part by balancing co-factors to facilitate host cell growth, metabolism, polypeptide production, and/or polypeptide activity. As disclosed herein, chlorite dismutase polypeptides catalyze the reaction converting chlorite ($ClO_2^-$) into chloride ($Cl^-$) and oxygen ($O_2$). As such, and without wishing to be bound to theory, it is further thought that a chlorite dismutase polypeptide of the present disclosure may influence the growth or output of the host cell by enzymatically generating intracellular oxygen, particularly under micro-aerobic conditions and/or conditions under which oxygen levels influence the balance of co-factors. Without wishing to be bound to theory, expression of a chlorite dismutase polypeptide of the present disclosure may therefore be particularly advantageous for a host cell that experiences stress under micro-aerobic conditions, for example a yeast cell of the present disclosure.

Methods to identify conditions where a chlorite dismutase polypeptide is expressed in a host cell are well known in the art. These methods may include, for example, growing a cell expressing a chlorite dismutase under a specific set of conditions in the presence of chlorite, and comparing its growth under identical conditions and chlorite levels to a corresponding cell of the same species that lacks chlorite dismutase. In other embodiments, additional suitable conditions may be identified by directly assessing the abundance of chlorite dismutase RNA or protein through standard methods known in molecular biology (Current Protocols in Molecular Biology, Ausubel et al., eds. Wiley & Sons, New York, 1988, and quarterly updates).

In some embodiments, the chlorite dismutase is expressed under the control of a constitutive promoter. Accordingly, in certain embodiments, a host cell is cultured under conditions whereby the promoter is sufficiently active to produce the desired amount or activity of chlorite dismutase polypeptide. In some embodiments, this desired amount may be empirically determined, for example, by measuring the growth of a host cell expressing the chlorite dismutase as a function of chlorite concentration in the growth medium.

In some embodiments, the chlorite dismutase is expressed under the control of an inducible promoter. Thus, in certain embodiments, the host cell is cultured under appropriate conditions to allow activation of the inducible promoter and subsequent production of chlorite dismutase polypeptide. For example, if the inducible promoter is activated by the addition of a metal, the host cell may be cultured in a culture medium containing the requisite amount of a suitable metal-containing compound that will allow activation of the promoter and sufficient expression of an operably linked chlorite dismutase polypeptide.

Fermentation

Certain aspects of the present disclosure relate to a host cell that produces a fermentation product. "Fermentation" refers to the metabolic process by which microorganisms convert a reduced carbon source into products including, without limitation, acids, alcohols, or gases without utilizing oxidative phosphorylation. Fermentation can either be an endogenous process in a host microorganism, or it may be an exogenous process that has been recombinantly engineered into a host microorganism. The enzymes that generate a fermentation product may be endogenous to the cell, or they may be exogenous proteins encoded by recombinantly expressed polynucleotides. One example of endogenous fermentation is the breakdown of glucose to yield ethanol and carbon dioxide. In some embodiments, a microorganism of the present disclosure contains one or more recombinant proteins necessary for the production of a fermentation product. In some embodiments, the necessary proteins may include, without limitation, one or more recombinant enzymes catalyzing any step in a chemical pathway that yields a desired product. In other embodiments, the one or more recombinant proteins may further include any protein that enhances the expression, stability, or activity of an enzyme, even if the protein itself does not possess catalytic activity.

In some embodiments, a host cell is cultured under conditions sufficient for the cell to produce a fermentation product. Conditions sufficient for a cell to produce a fermentation product are well known in the art and may be adapted depending upon the species of the cell, the desired product(s), or the scale of production. Fermentation may be executed on any scale of production, from a flask in a laboratory to large-scale industrial or commercial processing. Methods for fermentation on many scales are well known in the art (for example, see Villadsen, J. et al. Bioreaction Engineering Principles. $3^{rd}$ ed. Springer; 2011). In some embodiments, fermentation methods have been adapted for diverse applications including, without limitation, biofuel production, beer production, winemaking, protein purification, and synthesis of pharmaceutical products.

In some embodiments, the cell uses a carbon source as a substrate for fermentative metabolism. As used herein, a "carbon source" refers to a carbon-containing substrate or compound suitable for use by the microorganism for cell growth. Suitable carbon sources may include without limitation polymers, carbohydrates, acids, alcohols, aldehydes, ketones, amino acids, and peptides. Further examples of suitable carbon sources may include, without limitation, various monosaccharides such as glucose, arabinose, or xylose; oligosaccharides; disaccharides; polysaccharides; biomass polymers such as cellulose or hemicellulose; cellodextrins, such as cellobiose, cellotriose, etc.; saturated or unsaturated fatty acids; succinate; lactate; acetate; and ethanol, or mixtures of any of the preceding compounds. The carbon source can additionally be a product of photosynthesis, including, but not limited to glucose.

In some embodiments, a culture medium of the present disclosure may further include suitable minerals, salts, cofactors, buffers and other components known in the art that are suitable for the growth of the cells in culture and for the promotion of the enzymatic pathways that produce fermentation products. In other embodiments, the culture medium may be further supplemented with components that facilitate fermentation, including, without limitation, trace elements, growth factors, gases, chemical precursors, inducers, chelators, inhibitors, antibiotics and/or antimycotics, buffers, and antifoaming agents. In some embodiments, recombinantly engineered cells of the present disclosure are cultured under anaerobic conditions that promote fermentative metabolism.

A recombinantly engineered cell of the present disclosure may be grown by any culturing method known in the art, including, without limitation, batch culturing, fed-batch culturing, or continuous culturing. In some embodiments, a recombinantly engineered cell is grown in a bioreactor. The term "bioreactor" as used herein may refer to any vessel and its supporting components that contain the cell and its culture medium during fermentation. A bioreactor of the present disclosure may be of any size, shape, or design suitable for the particular application. In some embodiments, a suitable bioreactor includes, without limitation, a stirred-tank bioreactor. In some embodiments, a bioreactor of the present disclosure may contain one or more vessels, sensors for monitoring culture and microorganismal parameters, and control devices to alter the conditions and composition of the culture medium. Typically, bioreactors are closed to the outside environment, except for controlled inputs and outputs, to minimize introduction of additional contaminating microorganisms. In some embodiments, a recombinantly engineered cell of the present disclosure may be suspended in liquid culture medium within a bioreactor. In other embodiments, a recombinantly engineered cell may be fixed within the bioreactor. Suitable bioreactors for culturing fixed cells may include, without limitation, features such as plates, packed beds, moving beds, or membranes.

In some embodiments, the culture medium containing the cell is treated with chlorite prior to growing the cell in a bioreactor. In some embodiments, the chlorite treatment is carried out "off-line," or separate from fermentation. Examples of off-line treatment may include an organism recycle scheme, wherein a recombinantly engineered cell is removed from a bioreactor, treated with a chlorite solution (in a culture medium of the present disclosure, and while the cell is expressing a chlorite dismutase polypeptide of the present disclosure), and then re-introduced to a bioreactor for fermentation.

In some embodiments, the culture medium containing the cell is treated with chlorite while growing the cell in a bioreactor. In some embodiments, chlorite is added to the culture medium while the cell is fermenting in a bioreactor.

During fermentation, bioreactor conditions may be adjusted to affect the growth rate of the cultured host cell, for example by using continuous culture methods. Devices that continuously monitor and adjust particular parameters of the conditions in the bioreactor are well known in the art and include, without limitation, chemostats, auxostats, and turbidostats. Methods and devices for monitoring and controlling parameters such as temperature, pH, flow rates, dissolved gas levels, nutrient and waste levels, pressure, turbidity, agitation, and circulation are well known in the art (see, e.g., Villadsen, J. et al. Bioreaction Engineering Principles. $3^{rd}$ ed. Springer; 2011).

Fermentation Products

Certain aspects of the present disclosure relate to cells recombinantly engineered to express a chlorite dismutase polypeptide that are cultured under conditions sufficient for the cell to produce a fermentation product. As used herein, "fermentation products" may include compounds endogenously produced by fermentative metabolism of the host cell, or they may include compounds produced by the activity of recombinantly encoded polypeptides. Examples of suitable fermentation products include, without limitation, pharmaceutical compounds, commodity chemicals, plastics, biofuels, alcohols, oils, biodiesel, carbohydrates, amino acids, fatty acids and their esters, and precursors thereof. In some embodiments, the fermentation product of a recombinantly engineered cell may include hydrocarbons, hydrocarbon derivatives, ethanol, and butanol. "Hydrocarbon" as used herein refers to any compound solely composed of the elements carbon and hydrogen.

In some embodiments, cells of the present disclosure endogenously produce a fermentation product. Examples of suitable endogenous fermentation products include, without limitation, ethanol, lactic acid, and carbon dioxide. In some embodiments, recombinant engineering may enhance a cell's production of an endogenous fermentation product.

In other embodiments, a recombinantly engineered cell of the present disclosure further contains the proteins necessary to produce a fermentation product. In certain embodiments, the recombinantly engineered cell is further engineered to express one or more proteins necessary for the production of a fermentation product. In some embodiments, the fermentation product may result from a biochemical pathway that is engineered into the cell by recombinant polypeptide(s). In other embodiments, the fermentation product may result from a biochemical pathway in the cell that includes both endogenous and recombinant polypeptides. Recombinant proteins may participate in any step of fermentative metabolism. For example, recombinant proteins may allow a cell to utilize a carbon source that is not endogenously used by the cell for fermentation, such as xylose or cellobiose. Recombinant proteins may also allow a cell to transform a carbon source into a fermentation product that is not endogenously produced by the cell, such as butanol.

In some embodiments, a cell is further recombinantly engineered to produce a hydrocarbon or hydrocarbon derivative. In certain embodiments, suitable hydrocarbon derivatives may include ethanol or butanol. Examples of recombinantly engineering a host cell to produce a fermentation product, including hydrocarbons, hydrocarbon derivatives, ethanol, and butanol, are well known in the art (Tang, W. L. and Zhao, H. (2009). Biotechnol J 4(12): 1725-39). In one non-limiting example, a set of recombinant nucleic acid encoding an n-butanol production pathway, including the *Clostridium acetobutylicum* genes adhE2, bcd, crt, etfAB, hbd, and the *E. coli* atoB gene, can be introduced into recombinant cells to allow the cells to produce n-butanol from rich culture medium (Atsumi, S. et al. (2008). Metab Eng 10:305-11). In some embodiments, oils, such as fatty acid esters, can be produced by recombinantly engineered cells. For example, cells can be recombinantly engineered to express pyruvate decarboxylase and alcohol dehydrogenase and to lack acyl-CoA synthetase genes. In some embodiments, oil fermentation products can be further reacted with alcohols to produce biodiesel (see, e.g., Tang, W. L. and Zhao, H. (2009). Biotechnol J 4(12): 1725-39).

In certain embodiments, a recombinantly engineered cell of the present disclosure may contain a deletion of one or more endogenous genes whose encoded protein's activities compete or otherwise interfere with the production of a desired fermentation product. In one non-limiting example, it has been shown that the removal of msgA, cydAB, cyoABCD, and cbdAB genes in *E. coli*, along with expression of a recombinant ldhL from *Pediococcus acidilactici*, allows the production of D- and L-lactate under specific conditions (Tang, W. L. and Zhao, H. (2009). Biotechnol J 4(12): 1725-39).

Fermentation products may be purified by any suitable method known in the art. In some embodiments, fermentation products may be purified continuously, e.g., from a continuous culture. In other embodiments, fermentation products may be purified separately from fermentation, e.g., from a batch or fed-batch culture.

Chlorite Treatment

Chlorite-Containing Solution

Certain aspects of the present disclosure relate to the use of chlorite in the culture medium to reduce the growth rate or kill one or more contaminating microorganisms. As used herein, "chlorite" or "chlorite ions" refers to any solution or compound that contains a chlorite anion ($ClO_2^+$). "Chlorite" of the present disclosure may include any salt or acid containing the chlorite anion. Additionally, "chlorite" of the present disclosure may also include any solution containing any compound that can break down into or otherwise generate chlorite. Examples of compounds that may generate chlorite include, without limitation, any compound that contains a chlorate (any compound containing the $ClO_3^-$ anion), perchlorate (any compound containing the $ClO_4^-$ anion), or chlorine dioxide (the non-ionic $ClO_2$). It is well known in the art that such compounds may be chemically interconverted. For example, upon contact with water, sanitizing solutions with chlorine dioxide can undergo several oxidation-reduction reactions that generate chlorite, (per)chlorate, and chloride anions (EPA Guidance Manual, Chapter 4: Chlorine dioxide). The term "(per)chlorate" as used herein refers to any solutions or compounds that contain a chlorate or perchlorate anion.

Solutions and methods for using chlorite treatment as a disinfectant are well known in the art (see for example Bichai, F. and Barbeau, B. (2006). Water Qual Res J Canada 41(4):375-82). One non-limiting example of a chlorite solution of the present disclosure is sodium chlorite, which is sold in various formulations including SANOVA® Base, a 25% solution of sodium chlorite salt, for disinfecting food products (Technical Evaluation Report for the USDA National Organic Program: Acidified Sodium Chlorite. Jul. 21, 2008). In some embodiments, disinfecting solutions containing chlorite may further include other active or inert compound that aids or complements the disinfecting properties of the chlorite. One non-limiting example of this type of solution is acidified sodium chlorite, a disinfecting solution that contains chlorite and an acid, such as citric acid.

Another means known in the art for generating a chlorite solution of the present disclosure is by electrochemical generation (also known as a membrane electrolysis method). In this method, sodium chlorite is introduced into an electrochemical cell in an aqueous solution. Electrochemical energy applied to the cell catalyzes the formation of chlorine dioxide, which can be separated from the sodium chlorite and aqueous solution, for example by using a membrane. In some embodiments, chlorine dioxide may be generated, e.g., in the influent stream, by using the electrochemical method.

In some embodiments, a culture medium of the present disclosure is treated with chlorite of the present disclosure in an amount sufficient to reduce the growth rate or kill one or more contaminating microorganisms. In some embodiments, the amount used for treatment is dependent upon the parameters of the culture medium. For example, the volume, surrounding pH, and temperature of the culture medium may affect the amount sufficient to reduce the growth rate or kill one or more contaminating microorganisms. In some embodiments, the amount sufficient to reduce the growth rate or kill one or more contaminating microorganisms may further depend upon the pre-treatment growth rate, metabolic capabilities, pre-treatment amount, and specific species of the contaminating microorganisms. Methods for identifying the amount sufficient to reduce the growth rate or kill one or more contaminating microorganisms are well known in the art. For example, well-known assays may be used, such as a kill curve plotting the cell density (a measure of growth) of a particular microorganism as a function of chlorite concentration in the culture medium for a particular time interval of interest.

In some embodiments, the amount of chlorite sufficient to reduce the growth rate, kill, or otherwise inhibit one or more contaminating microorganisms may include, without limitation, at least 1 µM, at least 5 µM, at least 10 µM, at least 20 µM, at least 30 µM, at least 40 µM, at least 50 µM, at least 60 µM, at least 70 µM, at least 80 µM, at least 90 µM, at least 100 µM, at least 110 µM, at least 120 µM, at least 130 µM, at least 140 µM, at least 150 µM, at least 160 µM, at least 170 µM, at least 180 µM, at least 190 µM, at least 200 µM, at least 210 µM, at least 220 µM, at least 230 µM, at least 240 µM, at least 250 µM, at least 260 M, at least 270 µM, at least 280 µM, at least 290 µM, at least 300 µM, at least 310 µM, at least 320 µM, at least 330 µM, at least 340 µM, at least 350 µM, at least 360 µM, at least 370 µM, at least 380 µM, at least 390 µM, at least 400 µM, at least 410 µM, at least 420 µM, at least 430 µM, at least 440 µM, at least 450 µM, at least 460 µM, at least 470 µM, at least 480 µM, at least 490 µM, at least 500 µM, at least 510 µM, at least 520 µM, at least 530 µM, at least 540 µM, at least 550 µM, at least 560 µM, at least 570 µM, at least 580 µM, at least 590 µM, at least 600 µM, at least 610 µM, at least 620 µM, at least 630 µM, at least 640 µM, at least 650 µM, at least 660 µM, at least 670 µM, at least 680 µM, at least 690 µM, at least 700 M, at least 710 µM, at least 720 µM, at least 730 µM, at least 740 M, at least 750 M, at least 760 µM, at least 770 µM, at least 780 µM, at least 790 µM, at least 800 M, at least 810 M, at least 820 µM, at least 830 µM, at least 840 µM, at least 850 µM, at least 860 µM, at least 870 µM, at least 880 µM, at least 890 µM, at least 900 µM, at least 910 µM, at least 920 M, at least 930 µM, at least 940 µM, at least 950 µM, at least 960 µM, at least 970 µM, at least 980 µM, at least 990 µM, at least 1 mM, at least 1.5 mM, at least 2 mM, at least 2.5 mM, at least 3 mM, at least 3.5 mM, at least 4 mM, at least 4.5 mM, and at least 5 mM chlorite ion concentration. In some embodiments, the amount of chlorite sufficient to reduce the growth rate, kill, or otherwise inhibit one or more contaminating microorganisms is between about 10 µM and about 200 µM.

A solution containing chlorite of the present disclosure may be introduced to the culture medium at any time or stage of the culturing process, in the presence or absence of the recombinantly engineered cell. In certain embodiments, a culture medium is treated with chlorite prior to culturing a recombinantly engineered cell of the present disclosure. In some embodiments, the chlorite is added to the culture medium concurrently with the addition of a recombinantly engineered cell. In some embodiments, the chlorite is added to the culture medium intermittently during the culturing process. In some embodiments, the chlorite is produced continuously during culturing of a recombinantly engineered cell of the present disclosure. In some embodiments, the chlorite is continuously produced by electrochemical generation in the culture medium.

In some embodiments, a recombinantly engineered cell of the present disclosure is cultured in culture medium treated with chlorite under conditions whereby the chlorite dismutase polypeptide of the present disclosure is expressed. In certain preferred embodiments, the chlorite dismutase polypeptide is expressed and active when the cell is exposed to chlorite, thereby protecting the cell from the toxic effects of chlorite treatment.

Contaminating Microorganisms

As used herein, "contaminating microorganisms" refers to any microorganism present in the growth or fermentation medium other than the host cell that is cultured intentionally in the medium. As it contains all of the nutrients required to support the growth of desired microorganisms, culture medium may unintentionally serve to promote the growth of one or more contaminating microorganisms. Although hygienic process methods are designed to limit the exposure of the culture medium to contaminating microorganisms, in practice it is very difficult to ensure that one or more additional contaminating microorganisms will never be introduced into the culture medium, especially when cell culturing is performed on an industrial scale. Contaminating microorganisms are unwanted because they interfere with the growth and metabolism of the desired microorganisms through various means, such as by killing them, impairing their metabolism, competing with them for nutrients, or by secreting products that alter the metabolism of the fermentation microorganisms. They may further be unwanted because they chemically affect the growth medium or the desired fermentation product.

Examples of such "contaminating microorganisms" include, without limitation, prokaryotic microorganisms, bacteria, archaea, eukaryotic microorganisms, fungal cells, yeast, algae, and viruses, including bacteriophages. As used herein, the term "prokaryotic microorganisms" may refer to any microorganism that lacks a membrane-bound nucleus. Examples of prokaryotic microorganisms may include, without limitation, bacteria and archaea. As used herein, the term "bacteria" may refer to any microorganism within the domain of bacteria. As used herein, the term "archaea" may refer to any microorganism within the domain of archaea. As used herein, the term "eukaryotic microorganisms" may refer to any microorganism within the domain of eukaryota, including, without limitation, fungal cells, yeast, and algae. The terms "fungal cells" and "yeast" are described in paragraphs below. As used herein, the term "algae" may refer to any eukaryotic microorganism that contains chlorophyll, including for example phototrophic protists. As used herein, the term "bacteriophage" may refer to any virus that infects bacteria.

In some embodiments, the one or more contaminating microorganisms are from a bacterial species. In some embodiments, the contaminating bacteria may be members of a genus such as *Lactobacillus, Clostridium, Pediococcus, Enterococcus, Acetobacter*, and *Gluconobacter*. Contaminating microorganisms may also include bacteria or fungi, and they may represent any single species or any mixture of species from either the kingdom of bacteria or fungi.

In some embodiments, the contaminating microorganism is a bacteriophage. Bacteriophages are viruses that infect bacteria. Upon infecting a bacterial cell, they inject their DNA into the bacterium. After phage DNA entry into a bacterial cell, the phage can execute one of two pathways for propagation: the prophage or the lytic pathway. In the prophage pathway, the phage DNA is integrated into the bacterial chromosome and replicated along with it during cell division. In the lytic pathway, the phage uses bacterial cellular machinery to synthesize phage components (such as polypeptides and phage DNA) and eventually causes bacterial cell to lyse and thereby release viral particles to infect other bacterial cells. Phages in the prophage pathway may later be induced by environmental events to engage the lytic pathway (Alberts, B. et al. Molecular Biology of the Cell. $4^{th}$ ed. New York: Garland Science; 2002).

In some embodiments, the culture medium is treated with chlorite to reduce the growth rate, kill, or otherwise inhibit additional contaminating microorganisms. Due to the ability of bacteriophages to remain dormant during lysogeny inside bacteria (including bacteria expressing a chlorite dismutase polypeptide of the present disclosure), chlorite treatment may only be effective at killing or inactivating lytic bacteriophages. In the case of a contaminating bacteriophage, to reduce the growth rate, kill, or otherwise inhibit refers to reducing the incidence of bacterial infection and/or bacterial lysis by the bacteriophage.

The following examples are offered for illustrative purposes and to aid one of skill in better understanding the various embodiments of the disclosure. The following examples are not intended to limit the scope of the present disclosure in any way.

EXAMPLES

Example 1

Engineered Chlorite Resistance Through Expression of Chlorite Dismutase

Introduction

Large-scale fermentation-based biofuel production is moving towards scaling bioprocesses beyond anything previously conceived. However, solvent producing processes, such as ethanol fermentation by yeast, or acetone-butanol-ethanol fermentation by *Clostridium* species, are renowned for their susceptibility to contamination and bacteriophage infection. Although disinfectants, such as hypochlorite, chlorite, or chlorine dioxide, can be added to process waters to prevent infection, these same disinfectants would also be bactericidal against the process organism. However, if the process organism is engineered to heterologously express the chlorite dismutase enzyme that dismutates chlorite into chloride and oxygen, then it would be protected from the bactericidal effects of any chlorite added as a suitable disinfectant.

The chlorite dismutase is a well-characterized enzyme that is primarily found in perchlorate reducing bacteria (PRB), where it is a primary component of the respiratory pathway of the organism (Coates, J. D. & Achenbach, L. A. Nat Rev Micro 2, 569-580 (2004)). PRBs couple the oxidation of reduced substrates (organic carbon, $H_2$, $H_2S$, or Fe(II)) to the reduction of perchlorate to generate energy for growth. The perchlorate is initially reduced by the perchlorate reductase enzyme (Pcr) into chlorite, which is subsequently dismutated into chloride and molecular oxygen by the chlorite dismutase (Cld) (FIG. 1).

Figure 2:
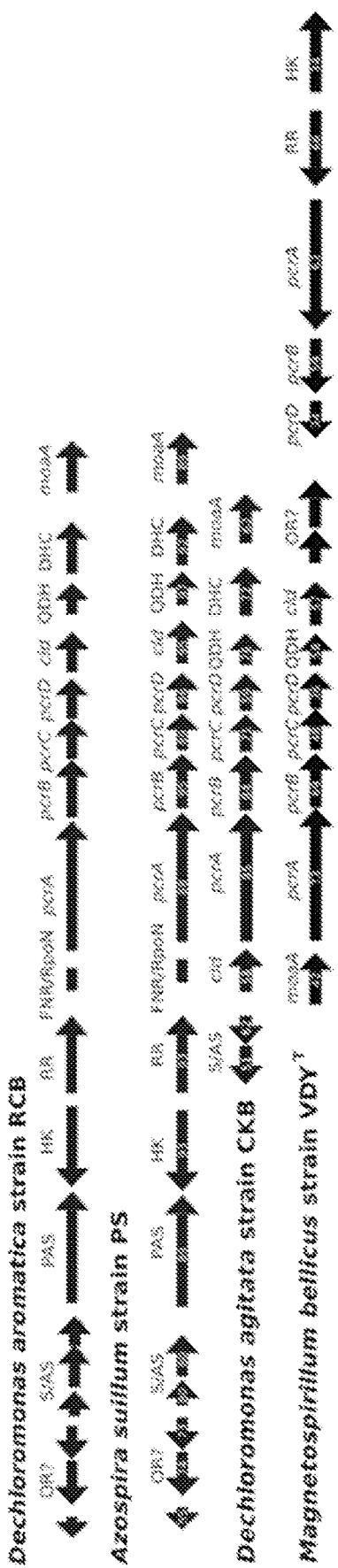
FIG. 2 depicts the structure of the conserved "core" of the perchlorate reduction genomic island (PRI). Four exemplary PRIs are shown (species of origin are as labeled); chlorite dismutase genes are labeled "cld."

Studies have identified the genes involved in this metabolism, demonstrated that this metabolism is the result of horizontal gene transfer, and by using comparative genomics have shown that this metabolism is encoded by a highly conserved perchlorate reduction genomic island (PRI) (FIG. 2) (Melnyk R A et al. (2011). Appl Environ Microbiol 77(20):7401-4).

Materials and Methods
Bacterial Strains and Plasmids

*Azospira suillum* PS (ATCC BAA-33/DSMZ 13638) was revived from a lab freezer stock and used as the wild-type strain for all genetic manipulations. Various *E. coli* strains were also used for cloning and conjugation purposes. Prior to all growth curves and genetic manipulations, all strains were streaked out from master freezer stocks to get single colonies.

Culture Conditions and Media

*E. coli* strains were grown in LB media. Kanamycin (Kan, 50 gig/mL) was used for selection and diaminopimelic acid (DAP, 0.3 mM) was used as a supplement to cultivate the auxotrophic strain WM3064. For routine culturing as well as growth assays, wild-type and mutant strains of PS were grown in ALP media. One liter of ALP media is composed of 0.49 g monobasic sodium phosphate dihydrate, 0.97 g dibasic anhydrous sodium phosphate, 0.1 g potassium chloride, 0.25 g ammonium chloride, 0.82 g sodium acetate, 2.0 g yeast extract, 7.6 g of a 60% w/w sodium lactate solution, 1.10 g sodium pyruvate and 10 mL of both vitamin mix and mineral mix. To make solid ALP media for plates, 15 g/L agar was added. Kanamycin was used for selection of PS mutants at a concentration of 50 gig/mL. For anaerobic growth of PS, ALP media was supplemented with either 5 mM sodium nitrate, 2.5 mM sodium perchlorate, or 5 mM of both sodium nitrate and sodium perchlorate. No growth was observed when no electron acceptor was added, confirming that PS is unable to grow via fermentation of the carbon sources present in ALP media. All strains of *E. coli* and PS were cultivated at 37° C. Anaerobic growth curves of PS for the transposon screen and characterization of strains was performed using a Spectramax 340PC384 plate reader in an anaerobic chamber (Coy Laboratory Products, Grass Lake, Mich.).

Results

Figure 3:
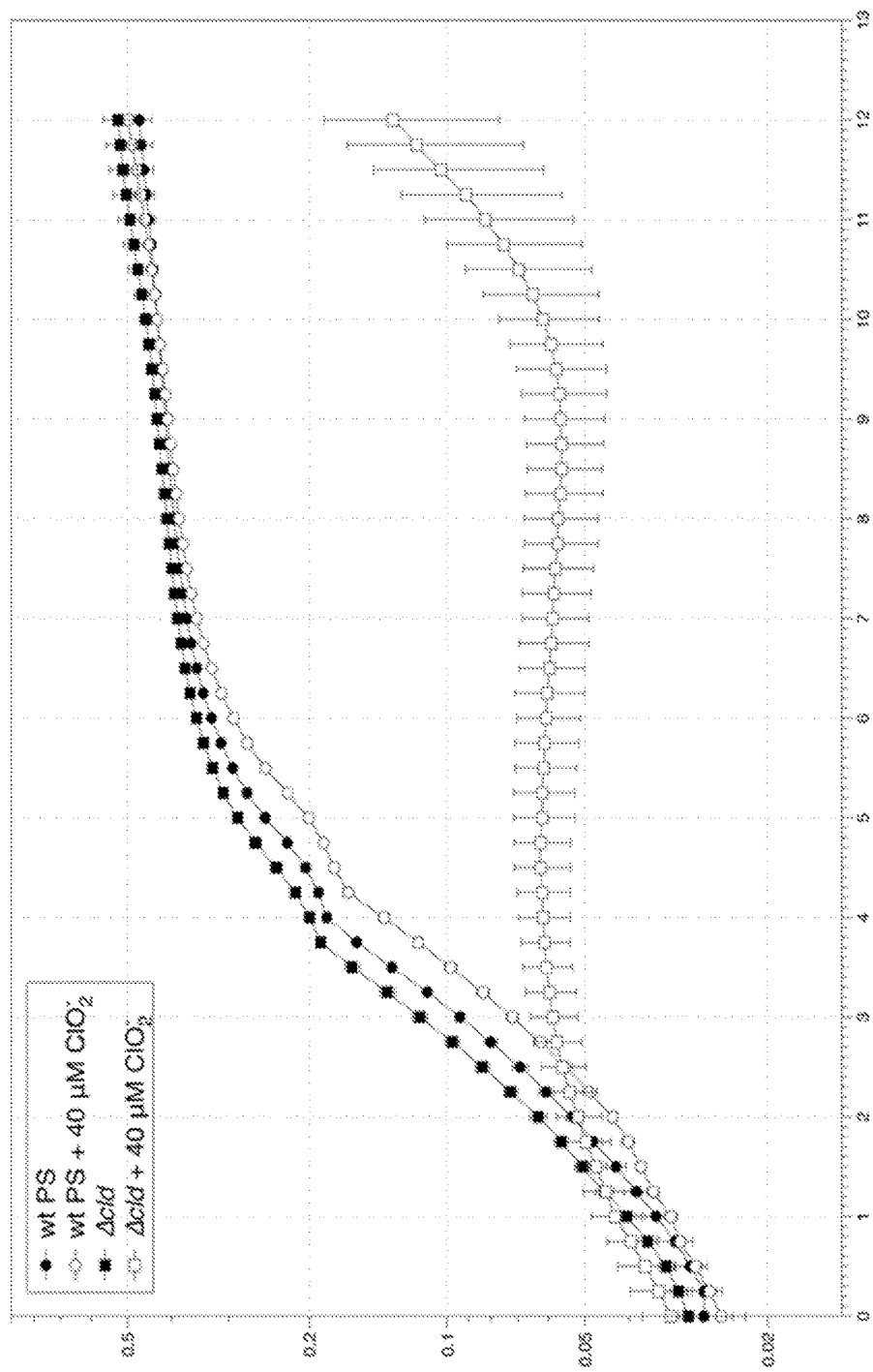
FIG. 3 depicts the aerobic growth of *Azospira suillum* strain PS grown in the presence or absence of 40 µM chlorite. The graph demonstrates the effect of chlorite with respect to growth on a wild-type (wt) strain, or a matched strain lacking the chlorite dismutase gene (Δcld). Four combinations are shown: wt strain grown in the absence of chlorite (dark circles), wt strain grown in the presence of 40 µM chlorite (open circles), Δcld strain grown in the absence of chlorite (dark squares), and Δcld strain grown in the presence of 40 µM chlorite (open squares).

A genetic system for studying the function of chlorite dismutase was established using the bacterial strain *Azospira suillum* strain PS (called "PS"). A deletion mutant was constructed, removing chlorite dismutase from this strain (Acid, based on the abbreviation for the chlorite dismutase gene, cld). Although this mutant has no growth defect when compared to the wild type strain PS when grown with oxygen as the sole electron acceptor, it is unable to grow with perchlorate or chlorate (FIG. 3).

However, the functional role of this enzyme goes beyond simply supporting a capacity to grow by perchlorate respiration by the host organism. The enzyme also plays a detoxification role for the host organism, protecting it against the bactericidal activity of chlorite in the environment. This is clearly shown by the significant increase in sensitivity to chlorite of the Δcld mutant compared to the wild type strain PS when grown aerobically in the presence of 40 µM chlorite (FIG. 3). Under this condition, no growth is observed for the Δcld mutant, while growth of the wild type strain is unimpaired in the presence or absence of chlorite.

Figure 4:
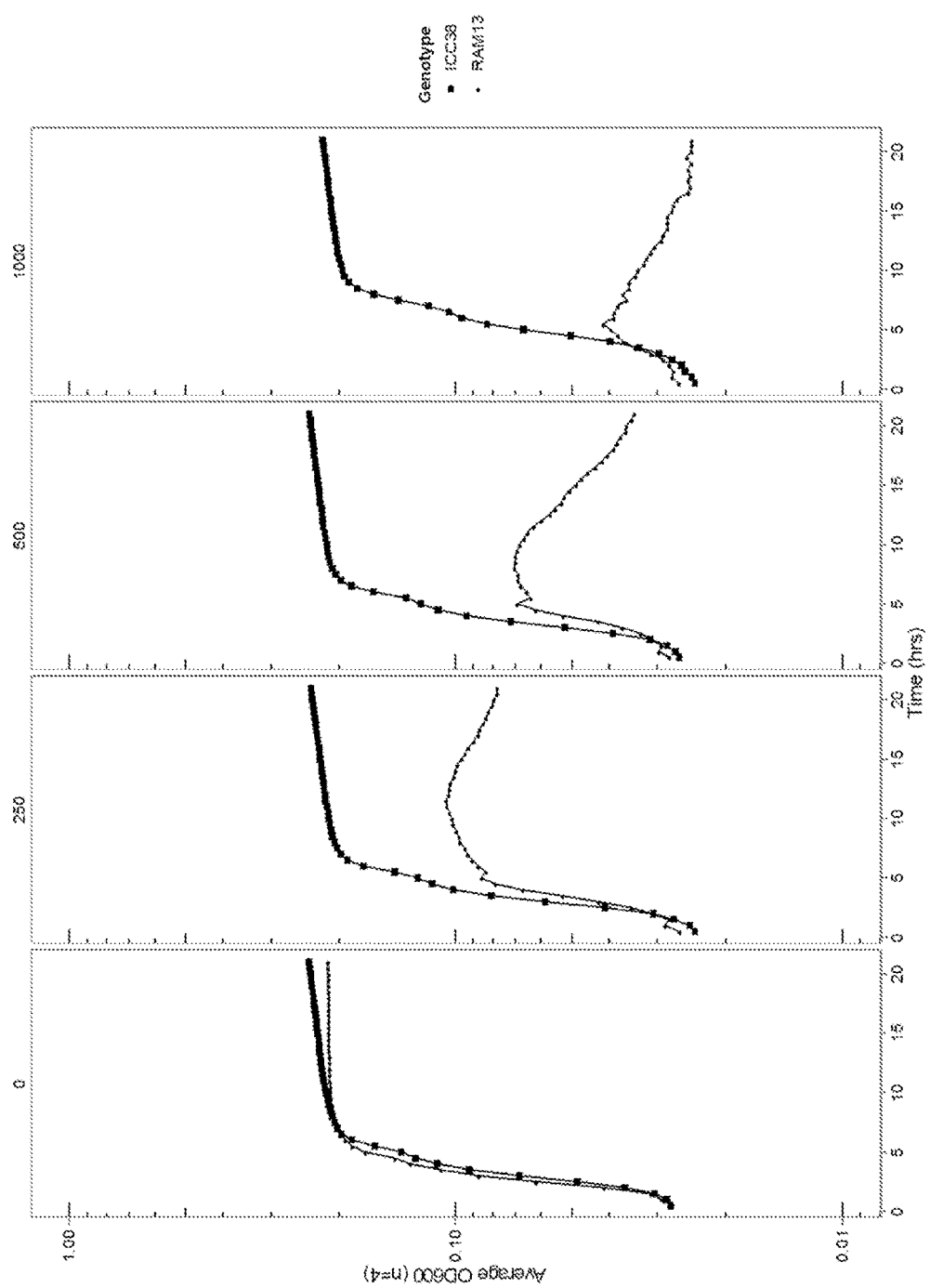
FIG. 4 depicts the aerobic growth of *Shewanella oneidensis* strain MR-1 in the presence of 0, 250, 500, or 1000 µM chlorite. Strain RAM13 (circles) contains an empty expression vector, while strain ICC38 (squares) is recombinantly engineered to constitutively express a chlorite dismutase.

To further demonstrate the protective effect of the chlorite dismutase to a host cell against chlorite, we recombinantly engineered *Shewanella oneidensis* strain MR-1 to constitutively express the heterologous cld gene from *Shewanella algae* ACDC. When the aerobic growth of the engineered strain (ICC38) in the presence of chlorite was compared to that of the wild type strain containing an empty expression vector (strain RAM13), recombinant chlorite dismutase expression clearly promoted the growth of the host cell (FIG. 4). In this instance, 250 µM chlorite was sufficient to cause a significant reduction in the growth rate on the wild type strain, whereas the growth of the recombinantly engineered strain was unimpaired (FIG. 4). Even at chlorite concentrations as high as 1000 µM, the recombinantly engineered strain showed minimal growth impairment, whereas the growth of the wild type strain was completely inhibited (FIG. 4).

These results clearly demonstrate that not only does chlorite dismutase play an important role in the respiratory pathway of perchlorate, but it also plays an important detoxification role in host cells. Its expression in an engineered strain endowed the host cell with the ability to withstand toxic levels of chlorite present in the growth medium. Such concentrations would prove inhibitory to more contaminating agents, such as bacteriophage, as it has recently been demonstrated that greater than 99% reduction in lytic phage particles can be achieved when the culture medium is treated with chlorite at a dose level of 15 mM (Bichai, F. and Barbeau, B. (2006). Water Qual Res J Canada 41(4):375-82).

Example 2

Chlorite Dismutase Expression Protects Cells from Levels of Chlorite Toxic to Contaminating Microorganisms Materials and Methods

*P. chloritidismutans* Growth Experiments

*Pseudomonas chloritidismutans*, a chlorate-reducing bacterium that expresses a native Cld protein (see, e.g., Wolterink, A. F., et al. (2002) Int. J. Syst. Evol. Microbiol. 52:183-90 and Mehboob, F., et al. (2009) FEMS Microbiol. Lett. 293:115-21), was grown in Luria Broth (LB). A sample of primary effluent from the East Bay Municipal Utility District water treatment plant was centrifuged at 4000×g for 20 minutes to remove debris and passed sequentially through a 0.45 µm filter and a 0.22 µm filter to remove particles and microbes. The clarified sample was incubated with *P. chloritidismutans* and plated in LB top agar to detect plaques. A plaque was transferred to a 25 ml culture of *P. chloritidismutans* and incubated until cell lysis was observed (5-6 hours) before centrifugation and filtration to obtain a working phage stock.

For growth experiments, *P. chloritidismutans* was grown in LB medium to an $OD_{600}$ of 0.233 (selected from a dilution series made from an overnight culture). The culture was diluted to $OD_{600}$=0.02, split into aliquots, and treated with 60 µM chlorite, and/or 50 µl phage stock, as appropriate (control included no added components). Each condition was replicated in six wells of a microtiter plate incubated at 37° C. Optical density (600 nm) was recorded during growth in a plate reader.

Caulobacter crescentus Growth Experiments

Wild-type *Caulobacter crescentus* NA1000 (Marks, M. E., et al. (2010) J. Bacteriol. 192:3678-88) was grown in peptone-yeast extract medium (PYE; see Ely, B. (1991) Methods Enzymol. 204:372-84) supplemented with 0.1% (v/v) ferrous sulphate/chelate solution (Sigma # F0518). The plasmid pJS14 is a derivative of the broad-host-range cloning vector pBBR1MCS (Kovach, M. E., et al. (1994) Biotechniques 16:800-2), which confers resistance to chloramphenicol. To express Cld from pJS14, the cld open reading frame from *P. chloritidismutans* was placed behind a ~430 base pair NcoI-EcoRI fragment of the xylX promoter from *C. crescentus* (Meisenzahl, A. C., et al. (1997) J. Bacteriol. 179:592-600). pJS14-xylX::cld or the empty vector pJS14 was transformed into NA1000 with selection using 1 μg/ml chloramphenicol.

The two strains were grown separately in PYE/chloramphenicol/ferrous sulphate supplemented with 0.3% xylose to induce cld expression. Each culture also received 1 mM chlorite, 4 mM chlorite, or no additional treatment, and the increase in optical density (660 nm) was measured over time in a microtiter plate reader. Each strain/condition was assayed in six individual wells.

*Caulobacter crescentus* NA 1000 harboring either pJS71 (KR260) or pJS14-xylX::cld (KR3557) were grown in PYE medium supplemented with 0.1% ferrous sulphate/chelate (Sigma # F0518) and 0.3% xylose to induce cld expression. pJS71 is a derivative of the broad-host-range plasmid pBBR1MCS (Kovach, M. E., et al. (1994) Biotechniques 16:800-2), which confers resistance to spectinomycin. The two strains were inoculated together at a 1:1 ratio in PYE/ferrous sulphate/xylose medium with or without 0.5 mM chlorite at 30° C. Samples were withdrawn from each co-culture at the indicated times, diluted, and plated on PYE medium supplemented with 1 μg/ml chloramphenicol or with 100 μg/ml spectinomycin to enumerate survivors of each species.

Measurement of Chlorite in Culture

KR260, KR3557, or a 1:1 mixture of the two strains were grown at 30° C. in PYE medium supplemented with 0.1% ferrous sulphate/chelate, 0.3% xylose, and 0.5 mM chlorite. Samples were withdrawn from each culture at the indicated times, and the chlorite concentration was measured using the colorimetric assay described in EPA Method 327.

Expression Vectors for Chlorite Dismutase or Heme Biosynthesis

The cd gene from *Pseudomonas chloritidismutans* DSM 13592 is cloned into a series of plasmids, such that each plasmid contains cld under the control of one promoter selected from pTDH3, pTEF1, pRPL18, pRNR2, and pREV1. Each of the plasmids contains a CEN6 element for stable transmission and complements a uracil auxotrophy with the URA3 gene. The host strain is BY4741 (MATa his3Δ1 leu2Δ0 met15Δ0 ura3Δ0).

hemE, hemN, hemG, and hemH genes from *Escherichia coli* are cloned into a plasmid under the control of a single promoter. The sequence of the ribosome binding site upstream of each gene may be varied to adjust expression levels of individual genes. The entire operon is integrated into the *C. acetobutylicum* chromosome of *C acetobutylicum* strain ATCC 824 using the described technique for homologous recombination (Heap, J. T., et al. (2012) Nucleic Acids Res. 40:e59).

In addition to the above *E. coli* genes, homologous genes from *Klebsiella pneumonia, Vibrio parahemolyticus* (particularly as these contain HemG rather than HemY), *Bacillus subtilis, Listeria monocytogenes, Staphylococcus epidermidis, Streptococcus mutans*, or from Gram-positive firmicutes more closely related to *C. acetobutylicum* may also be tested.

Results

To demonstrate that chlorite dismutase expression may protect cells from levels of chlorite that inactivate contaminating agents such as bacteriophages, a naturally chlorate-reducing strain of *Pseudomonas chloritidismutans* was tested. This strain is known to express chlorite dismutase. An as-yet uncharacterized bacteriophage that attacks this strain was isolated from a MUD anaerobic sludge digester.

Figure 5:
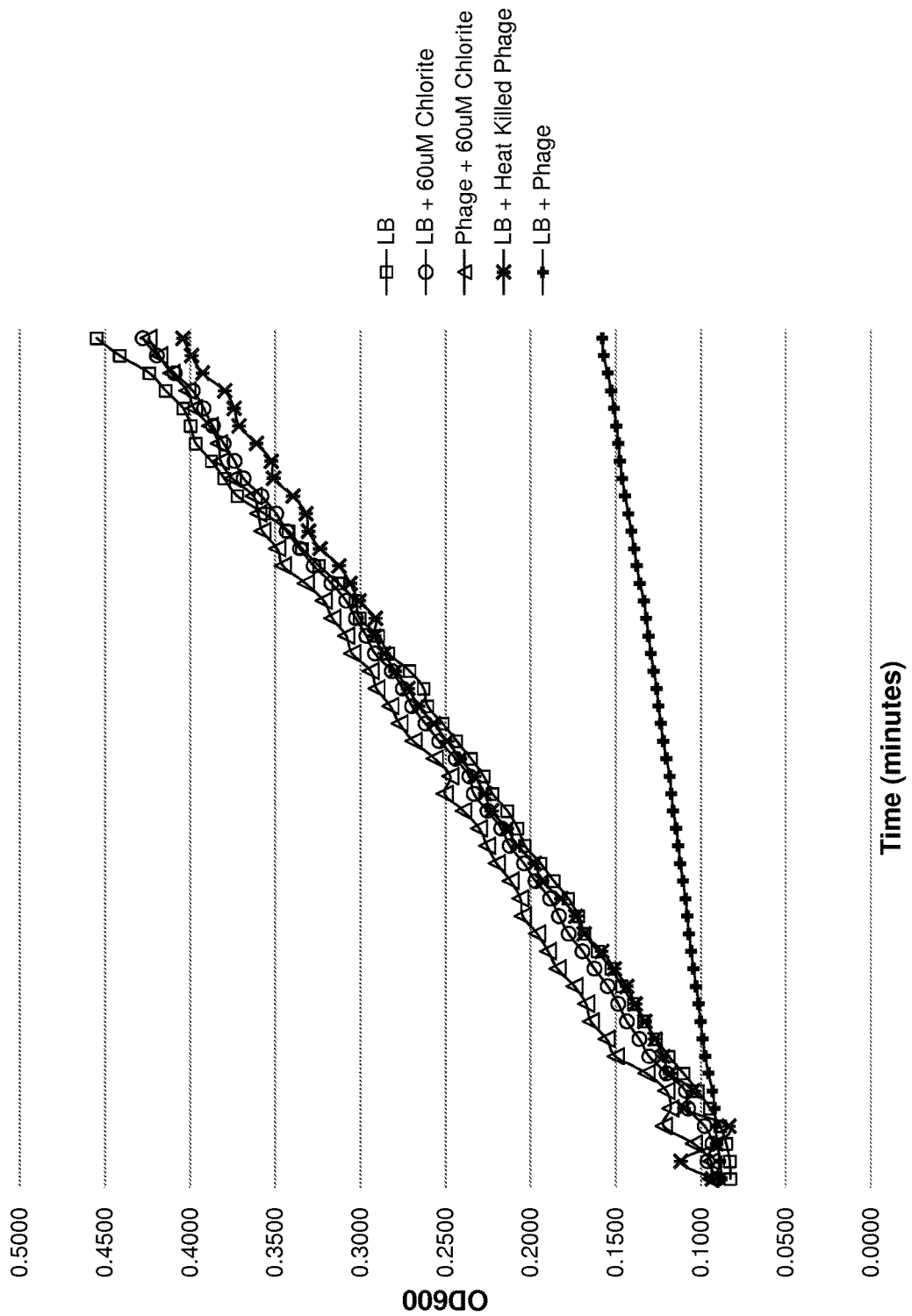
FIG. 5 demonstrates that culturing a bacterial strain expression chlorite dismutase in chlorite protects the strain from phage-mediated killing. The growth of *Pseudomonas chloritidismutans* (as shown by $OD_{600nm}$) over time is depicted for cultures grown in LB alone (squares), LB plus 60 µM chlorite (circles), LB plus 60 µM chlorite plus phage (triangles), LB plus heat-killed phage (asterisks), and LB plus phage (pluses).

The growth of this *P. chloritidismutans* strain was tested in the presence and absence of chlorite. As shown in FIG. 5, it was observed that 60 μM chlorite alone did not hinder the growth of *P. chloritidismutans*, nor did the heat-killed phage. Live phage blocked the growth of *P. chloritidismutans*, but importantly, the addition of chlorite and phage together resulted in a wild-type growth rate. This result demonstrates that the combination of Cld expression and chlorite addition can protect *P. chloritidismutans* from phage-mediated killing.

Figure 6:
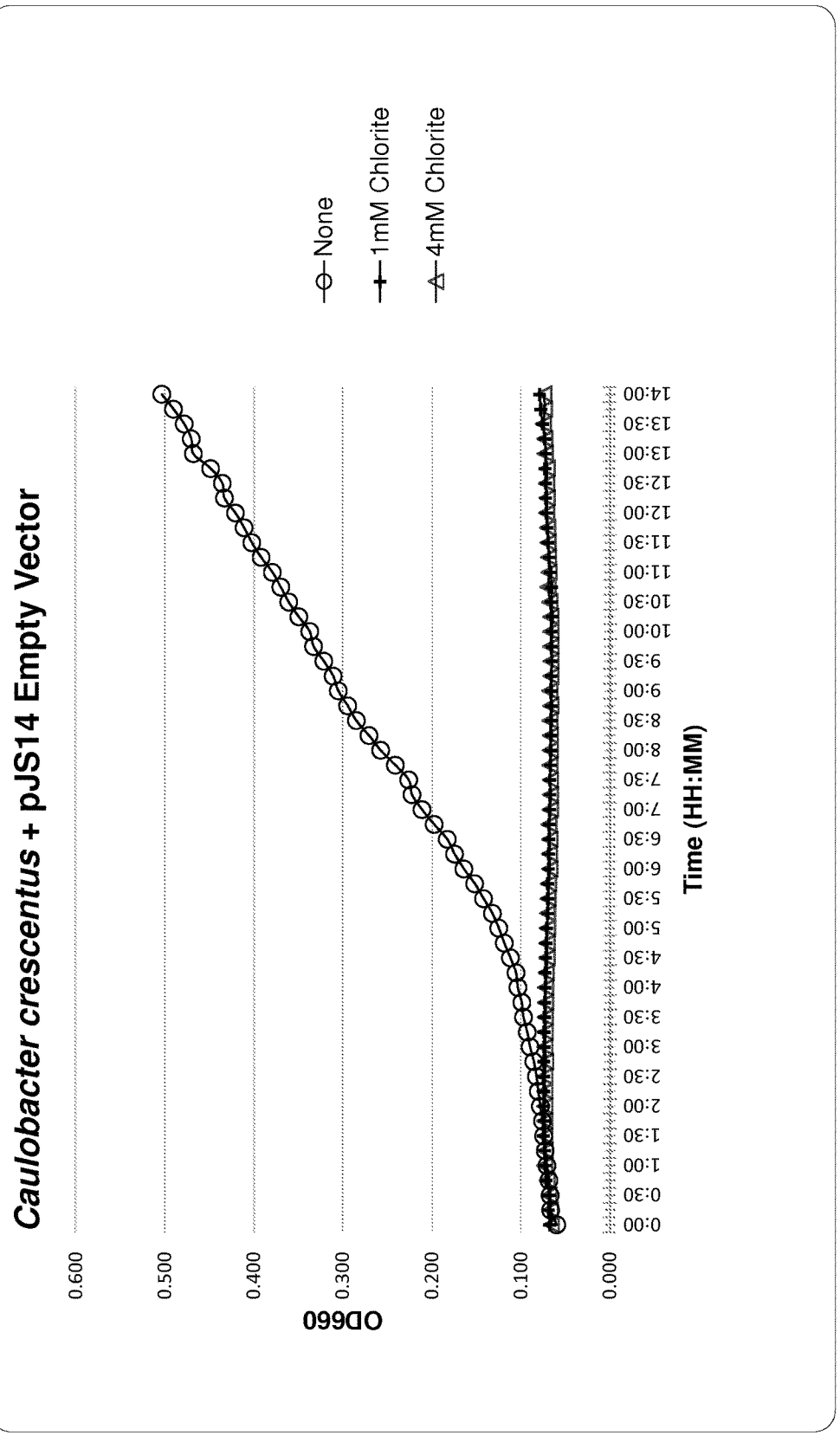
FIG. 6 depicts the growth of wild-type *Caulobacter crescentus* bearing an empty plasmid (pJS14) in medium supplemented with 1 mM (pluses) or 4 mM chlorite (triangles), as compared to medium with no chlorite (circles).
Figure 7:
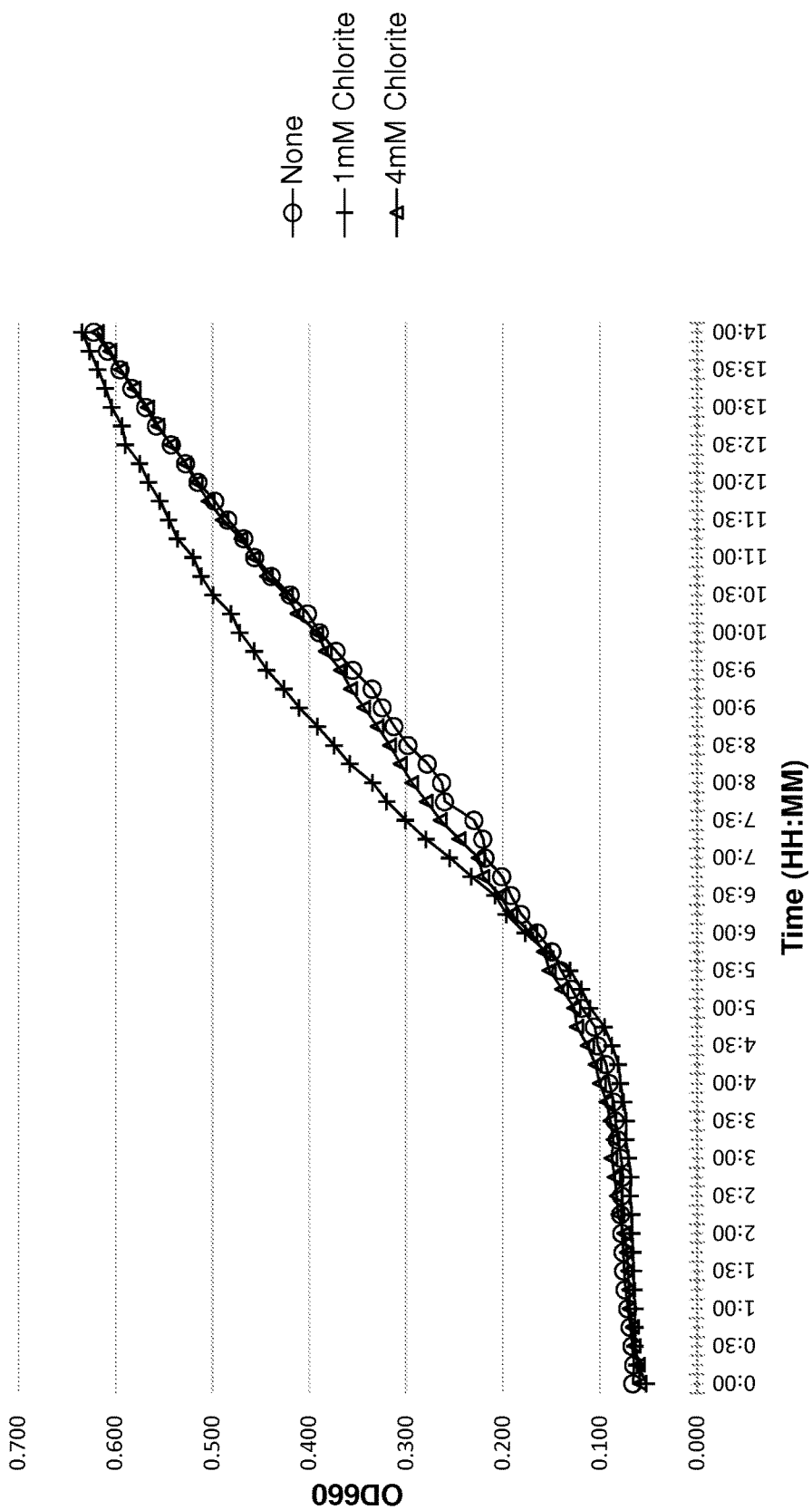
FIG. 7 depicts the growth of wild-type *Caulobacter crescentus* bearing a plasmid expressing chlorite dismutase under the control of a xylose-inducible promoter (pJS14-xylX::cld) in medium supplemented with 1 mM (pluses) or 4 mM chlorite (triangles), as compared to medium with no chlorite (circles).

Because *P. chloritidismutans* growth was not completely inhibited by the bacteriophage, and to test this approach in a bacterium that does not endogenously express chlorite dismutase, chlorite dismutase from *A. suillum* PS was expressed in the oligotrophic alpha-proteobacterium *Caulobacter crescentus*. The growth of wild-type *Caulobacter* was completely blocked in the presence of 1 mM or 4 mM chlorite (FIG. 6). However, when chlorite dismutase expression by introduced into this *Caulobacter* strain on a medium-copy plasmid under the control of a xylose-inducible promoter, the strain was resistant to both 1 mM and 4 mM chlorite, growing at the same rate in medium with 1 mM or 4 mM chlorite as compared to control medium lacking chlorite (FIG. 7). Therefore, while both concentrations of chlorite killed *C. crescentus* cells harboring pJS14, the strain expressing Cld grew at nearly wild-type rates in either 1 mM or 4 mM chlorite, indicating that Cld expression protects *C. crescentus* from the toxic effects of chlorite. These results demonstrate that heterologous expression of chlorite dismutase in a cell that does not normally express the enzyme protects the growth of the cell from chlorite toxicity. It was noted that *Caulobacter* cells expressing chlorite dismutase did not grow well unless the medium was supplemented with chelated ferrous iron, suggesting the presence of iron may be required for activity of the heme-containing chlorite dismutase.

Next, the ability of chlorite to kill or inhibit the growth of non-chlorite dismutase-expressing contaminants was tested. *Caulobacter* strains KR260 (empty plasmid) and KR3557 (chlorite dismutase expression plasmid) were co-cultured in the presence of 0.5 mM chlorite. In the co-culture, the presence of empty plasmid (containing a spectinomycin resistance marker) or chlorite dismutase expression plasmid (containing a chloramphenicol resistance marker) was not selected. Rather, both strains were co-cultured in PYE medium without selection, samples were taken, and the number of surviving colonies that were resistant to spectinomycin (KR260) or chloramphenicol (KR3557) were counted at the indicated times (FIG. 8).

Figure 8:
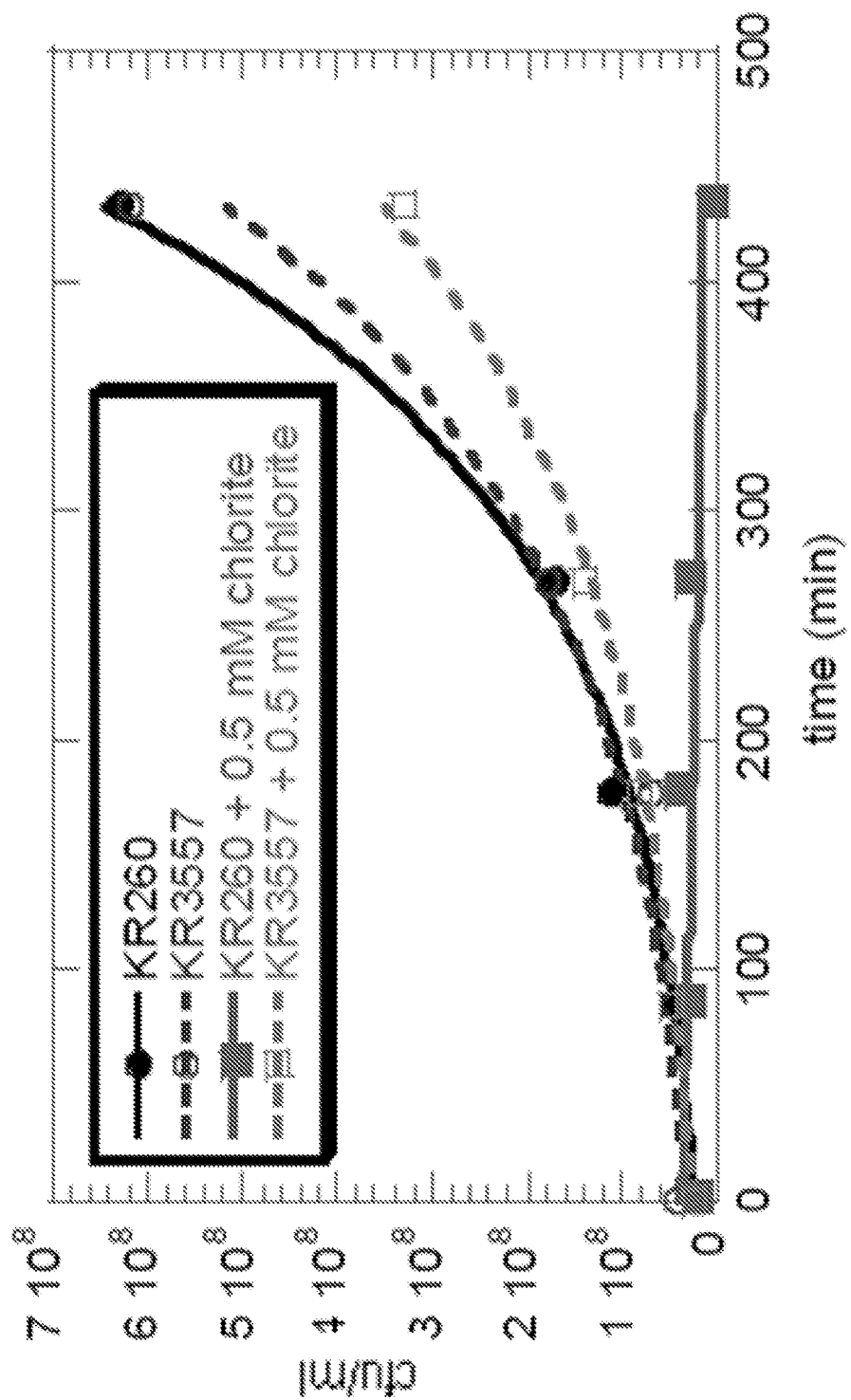
FIG. 8 shows the results of competition experiments where a chlorite dismutase-expressing *Caulobacter* strain (KR3557) and a non-chlorite dismutase-expressing *Caulobacter* strain (KR260) were co-cultured in the presence or absence of 0.5 mM chlorite. Growth of each strain was observed over time by measuring cfu/mL.

In the culture without chlorite, KR260 and KR3557 grew and divided at similar rates, while in the culture containing chlorite, KR3557 grew at a slightly reduced rate, and the growth of KR260 was completely blocked (FIG. 8). This experiment demonstrates that in the presence of chlorite, Cld-expressing bacteria can be selectively spared, while the growth of bacteria lacking Cld is greatly inhibited.

Figure 9:
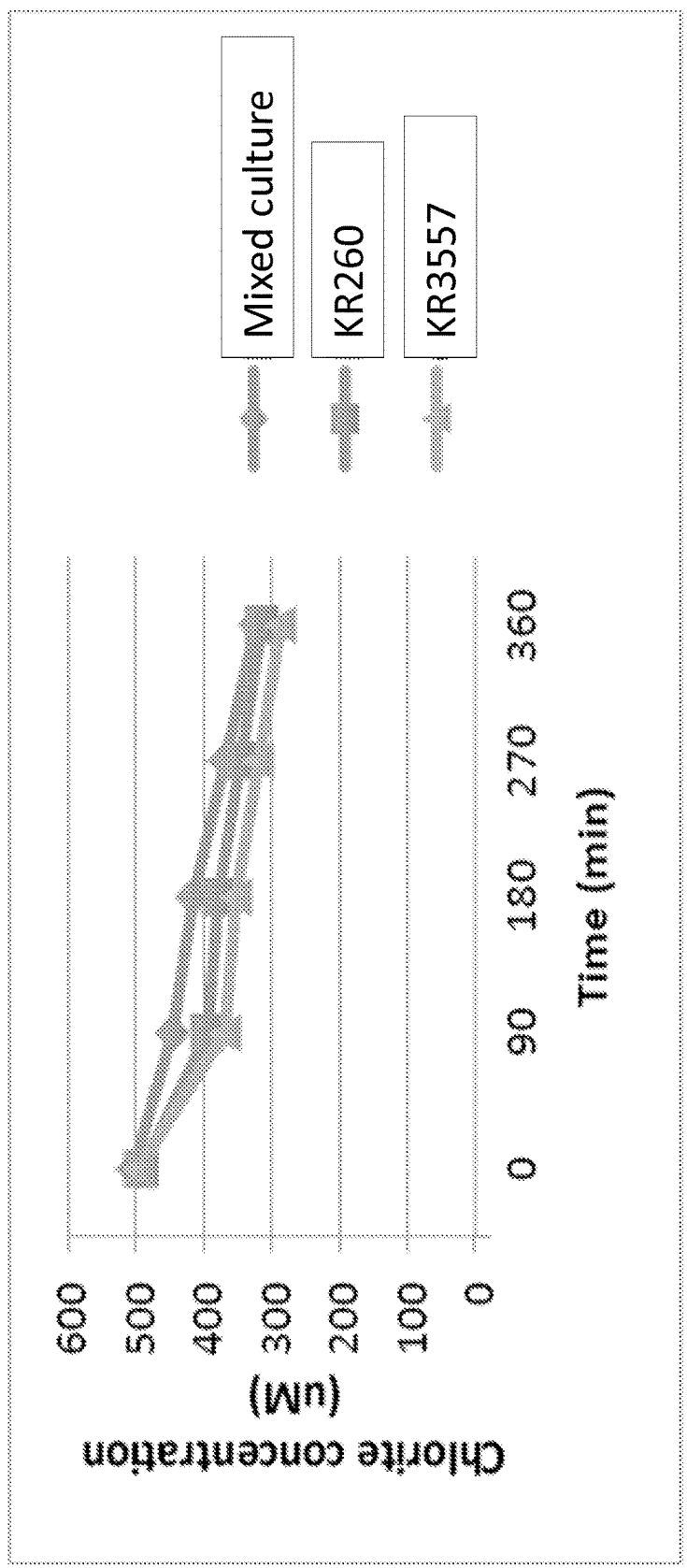
FIG. 9 plots the concentration of chlorite present in cultures over time. Cultures included a chlorite dismutase-expressing *Caulobacter* strain (KR3557), a non-chlorite dismutase-expressing *Caulobacter* strain (KR260), or a mixed culture of both strains.

Because the above experiments were performed in batch culture, the concentration of chlorite present in the medium was examined over time to determine how quickly added chlorite is cleared from cultures of chlorite dismutase-expressing or non-expressing strains. Control KR260 and chlorite dismutase-expressing strain KR3557 were cultured individually and together in a starting concentration of 500 µM chlorite (FIG. 9). As shown in FIG. 9, the rate of chlorite disappearance was similar in the three cultures, even though one culture (KR260) contained no organisms with Cld activity. Also, the chlorite did not immediately react to form other products upon addition to the culture medium, as ~0.3 mM chlorite was still present in each culture after a period of six hours.

These results demonstrate that chlorite dismutase expression protects host cells from levels of chlorite that are sufficient to inactivate contaminating microorganisms, such as bacteriophages and non-chlorite dismutase-expressing bacteria.

Example 3

Vectors for Expression of Chlorite Dismutase

The previous Example demonstrates that chlorite dismutase expression may be used as a tool to reduce the growth of or kill contaminating microorganisms, including bacteriophages and bacterial strains. In order to apply this discovery to a variety of process organisms of interest, there is a need for expression vectors to express chlorite dismutase and related enzymes at appropriate levels.

Figure 10:
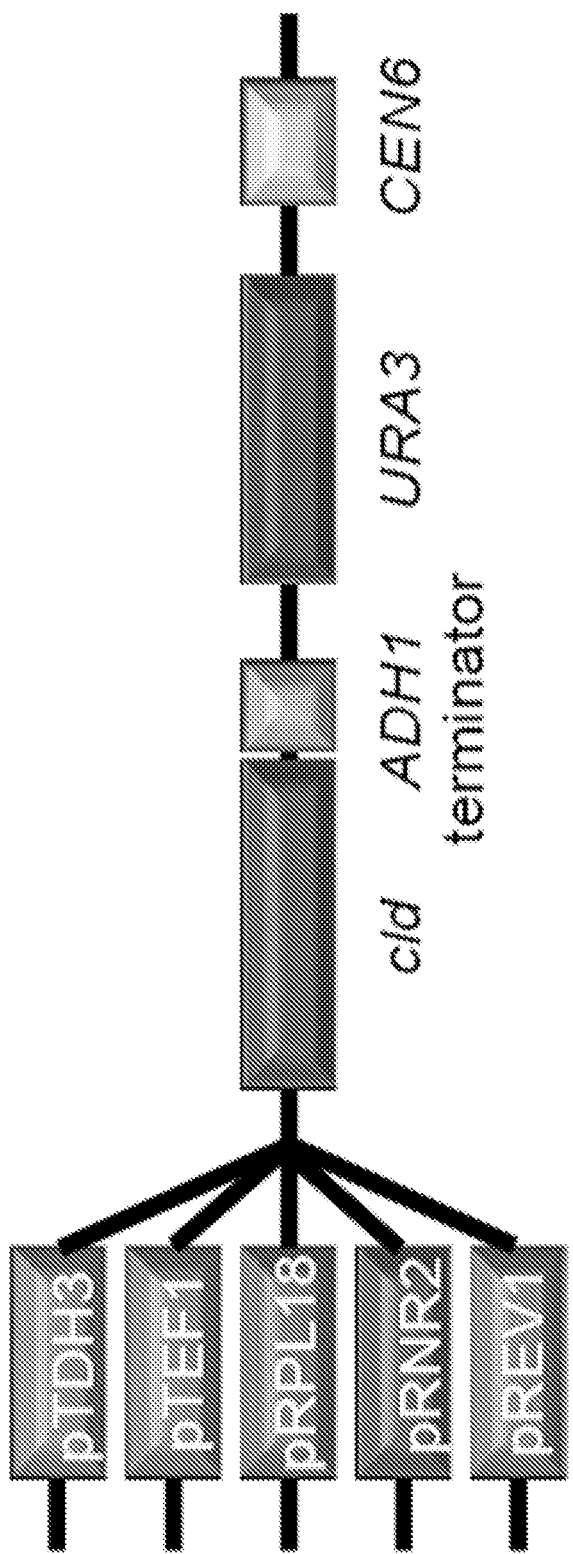
FIG. 10 illustrates a set of centromere-based yeast plasmids designed to express chlorite dismutase at different levels.

To meet this need, a set of centromere-based plasmids designed to express chlorite dismutase at different levels in Saccharomyces cerevisiae is designed. As depicted in FIG. 10, all of these expression plasmids contain a promoter, chlorite dismutase coding sequence coupled to the ADH1 terminator, a selectable marker (e.g., URA3), and a centromere sequence (e.g., CEN6). Exemplary promoters include pTDH3, pTEF1, pRPL18, pRNR2, and pREV1. Each plasmid is transformed into S. cerevisiae strains BY4741 and BY4742, as well as industrially relevant strains. For each transformant, chlorite sensitivity is measured under aerobic and anaerobic conditions, and cell extracts are tested for chlorite dismutase expression by Western blotting.

Chlorite sensitivity in unmodified yeasts and in those expressing Cld are measured first in aerobic batch culture with concentrations of chlorite up to 20 mM. Growth is measured as an increase in optical density (600 nm). If a strain expressing Cld is found to have increased tolerance to one or more concentrations of chlorite, the growth of the same unmodified and Cld-expressing strains in anaerobic fermentation conditions will be measured, with and without added chlorite. To distinguish between blocked growth and cell killing, colony-forming units on plates lacking chlorite are measured during each of the growth experiments described above.

Chlorite dismutase expression is also tested in industrial fermenting strains, such as Clostridium strains (e.g., C. acetobutylicum) that perform acetone-butanol-ethanol fermentation. However, Clostridium strains are obligate fermenters that do not naturally produce cytochromes or heme. An exemplary pathway for heme biosynthesis is provided in FIG. 11. C. acetobutylicum contains genes encoding a partial heme biosynthesis pathway, covering reactions 1-3 in FIG. 11. This partial pathway leads to the production of the heme intermediate uroporphyrinogen III, which is subsequently converted to siroheme or corrinoids.

Clostridium acetobutylicum ATCC 824 contains the genes encoding HemB, HemC, and HemD, which together convert aminolevulinic acid to uroporphyrinogen III. However, C. acetobutylicum lacks genes for the enzymes that convert uroporphyrinogen III to protoheme IX. The first step in the pathway, catalyzed by HemE, converts uroporphyrinogen III to coproporphyrinogen III and carbon dioxide. The second step, catalyzed either by HemN or HemF, converts coproporphyrinogen III to protoporphyrinogen IX and carbon dioxide. The third step, catalyzed by HemG or HemY, converts protoporphyrinogen IX to protoporphyrin IX. The final step, catalyzed by HemH, adds iron to protoporphyrin IX to form protoheme IX. Step 2 can be catalyzed by an oxygen-dependent enzyme (HemF) or an oxygen-independent enzyme (HemN). Step 3 can also be catalyzed by oxygen-dependent (HemY) or oxygen-independent (HemG) enzymes. The oxygen-independent enzyme in each case may be tested first, in keeping with the fermentative lifestyle of C. acetobutylicum.

Figure 11:
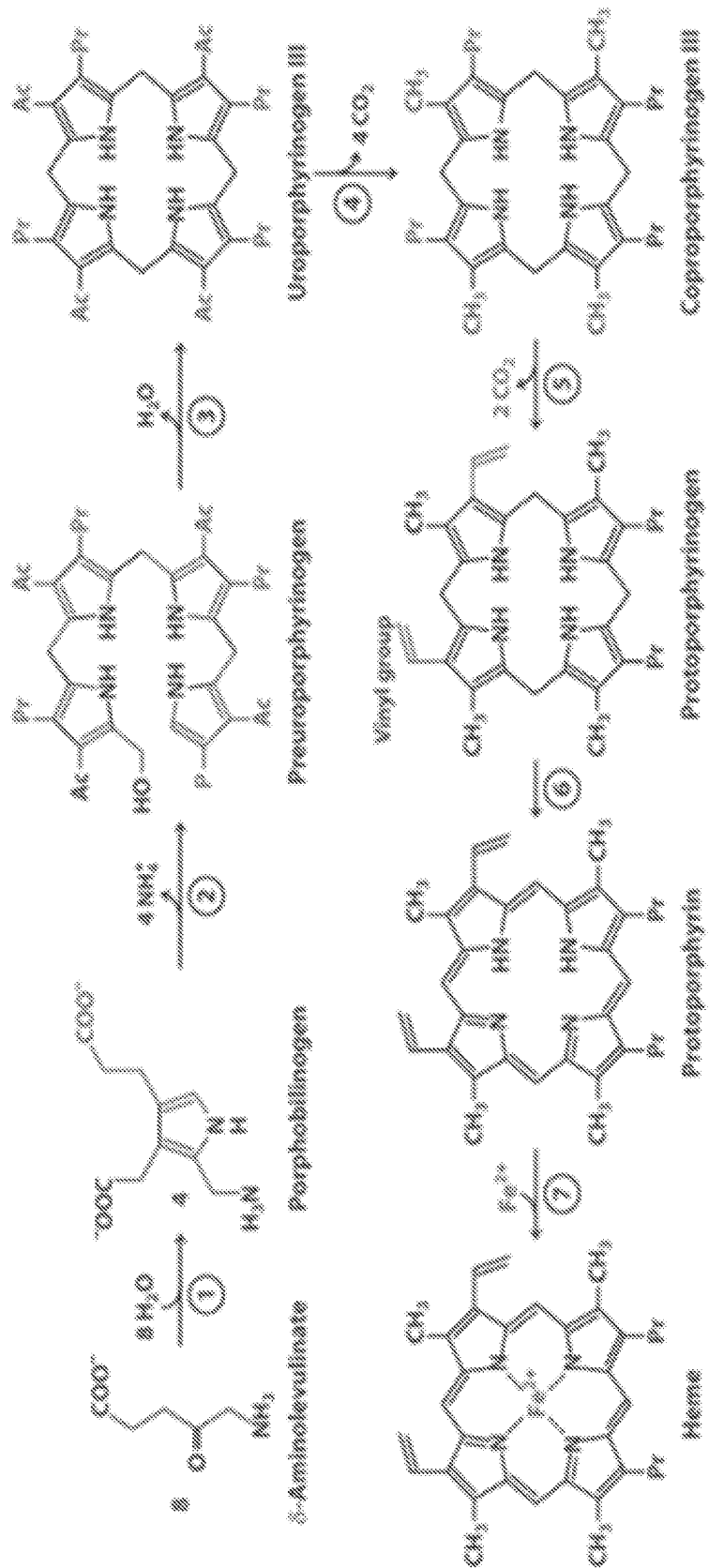
FIG. 11 illustrates an exemplary pathway for heme biosynthesis in bacteria.

To express a functional, heme-containing chlorite dismutase in Clostridium, enzymes that catalyze reactions 4-7 in FIG. 11 are expressed. As described above, step 4 is catalyzed by uroporphyrinogen III decarboxylase, encoded by hemE. Step 5 is catalyzed by coproporphyrinogen III oxidase (CPO). The C. acetobutylicum genome appears to encode two copies of the oxygen-independent CPO hemN, although their expression and function in C. acetobutylicum has not been tested. Step 6 is catalyzed by protoporphyrinogen IX oxidase, which is present in oxygen-dependent and -independent (e.g., hemG) forms. Step 7 is catalyzed by ferrochelatase (e.g., hemH).

Constructs for expressing these enzymes are generated and integrated into C. acetobutylicum as described above. As sources for the genes in these pathways, the hemE, hemN, hemG, and hemH genes from Escherichia coli are tested first. Without wishing to be bound to theory, it is thought that these enzymes have coevolved in the same organism and thus may work better together than enzymes from disparate sources. However, genes from other Gram-negative organisms such as Klebsiella pneumoniae and Vibrio parahemolyticus (particularly as these contain HemG rather than HemY), or from Gram-positive firmicutes more closely related to C. acetobutylicum may also be used. Non-limiting examples of firmicute species containing some or all of the relevant genes include Bacillus subtilis, Listeria monocytogenes, Staphylococcus epidermidis, and Streptococcus mutans, as described herein.

Recombinant C acetobutylicum strain(s) are grown and tested under anaerobic conditions. The presence of heme, porphyrins, and/or heme pathway intermediates in C. acetobutylicum strains expressing a heme biosynthesis pathway is measured in extracts using two methods: reverse-phase chromatography followed by thin-layer chromatography (Hansson M. and Hederstedt L. (1994) J. Bacteriol. 176: 5962-70), and high-performance liquid chromatography (Franken A C W et al. (2013) Appl. Microbiol. Biotechnol. 97:9773-85). Production of chlorite dismutase protein in C. acetobutylicum strains expressing a heme biosynthesis pathway is monitored using a chlorite dismutase antibody. Heme bound to chlorite dismutase expressed in C. acetobutylicum strains expressing a heme biosynthesis pathway is detected and quantified (Nygaard T K et al. (2006) BMC Microbiol.

6:82). Methods will be used to determine if the strain(s) perform solventogenic fermentation in the presence of added chlorite.

Tolerance to chlorite in the culture medium is tested by growing a *C. acetobutylicum* strain expressing a heme biosynthesis pathway and a chlorite dismutase in varying concentrations of chlorite (as described above), as compared to growth in culture medium lacking chlorite. These growth rates are compared to the growth rate of a *C. acetobutylicum* strain lacking one or more components of the heme biosynthesis pathway and/or the chlorite dismutase (e.g., a strain that lacks the appropriate coding sequence, or a strain in which expression of the appropriate coding sequence has not been induced) grown in culture medium with the same concentrations of chlorite. ABE fermentation in a *C. acetobutylicum* strain expressing a heme biosynthesis pathway and a chlorite dismutase grown in a cell culture medium with varying concentrations of chlorite is compared with ABE fermentation of the same strain in cell culture medium lacking chlorite. ABE fermentation of this strain is also compared with the ABE fermentation of a *C. acetobutylicum* strain lacking one or more components of the heme biosynthesis pathway and/or the chlorite dismutase (e.g., a strain that lacks the appropriate coding sequence, or a strain in which expression of the appropriate coding sequence has not been induced) grown in culture medium with the same concentrations of chlorite.

I claim:

1. A method of culturing a cell, comprising:

a) culturing a cell recombinantly engineered to express a functional chlorite dismutase in a culture medium under conditions whereby the chlorite dismutase is expressed in said cell, wherein said culture medium comprises one or more contaminating microorganisms, wherein the chlorite dismutase is expressed in the cell from a chlorite dismutase gene (cld) heterologous to the cell; and b) treating said culture medium with chlorite in an amount sufficient to kill said one or more contaminating microorganisms without killing said cell, wherein the chlorite dismutase protects the cell from toxic effects of the chlorite.

2. The method of claim 1, wherein the cld is a perchlorate-reducing bacterium gene.

3. The method of claim 1, wherein the cell does not naturally express a chlorite dismutase.

4. The method of claim 1, wherein the cell is a bacterial call selected from *Acidobacteria, Actinobacteria, Aquificae, Armatimonadetes, Bacteroidetes, Caldiserica, Chlamydiae, Chlorobi, Chloroflexi, Chrysiogenetes, Cyanobacteria, Deferribacteres, Deinococcus-thermus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.*

5. The method of claim 2, wherein the cell is a bacterial call selected from *Acidobacteria, Actinobacteria, Aquificae, Armatimonadetes, Bacteroidetes, Caldiserica, Chlamydiae, Chlorobi, Chloroflexi, Chrysiogenetes, Cyanobacteria, Deferribacteres, Deinococcus-thermus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.*

6. The method of claim 3, wherein the cell is a bacterial call selected from *Acidobacteria, Actinobacteria, Aquificae, Armatimonadetes, Bacteroidetes, Caldiserica, Chlamydiae, Chlorobi, Chloroflexi, Chrysiogenetes, Cyanobacteria, Deferribacteres, Deinococcus-thermus*, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.

7. The method of claim 1, wherein the cell is a fungal cell selected from Ascomycota and Basidiomycota.

8. The method of claim 2, wherein the cell is a fungal cell selected from Ascomycota and Basidiomycota.

9. The method of claim 3, wherein the cell is a fungal cell selected from Ascomycota and Basidiomycota.

10. The method of claim 1, wherein the cell is selected from *Saccharomyces* sp., *Trichoderma reesei, Neurospora* sp., *Kluyveromyces* sp., *Pichia* sp., *Sporotrichum* thermophile, *Candida shehatae, Candida tropicalis, Neurospora crassa, Zymomonas mobilis, Clostridium* sp., *Moorella thermoacetica, Escherichia coli, Klebsiella oxytoca, Thermoanaerobacterium saccharolyticum, Yarrowia* sp., and *Bacillus* sp.

11. The method of claim 2, wherein the cell is selected from *Saccharomyces* sp., *Trichoderma reesei, Neurospora* sp., *Kluyveromyces* sp., *Pichia* sp., *Sporotrichum thermophile, Candida shehatae, Candida tropicalis, Neurospora crassa, Zymomonas mobilis, Clostridium* sp., *Moorella* thermoacetica, *Escherichia coli, Klebsiella oxytoca, Thermoanaerobacterium saccharolyticum, Yarrowia* sp., and *Bacillus* sp.

12. The method of claim 3, wherein the cell is selected from *Saccharomyces* sp., *Trichoderma reesei, Neurospora* sp., *Kluyveromyces* sp., *Pichia* sp., *Sporotrichum thermophile, Candida shehatae, Candida tropicalis, Neurospora crassa, Zymomonas mobilis, Clostridium* sp., *Moorella* thermoacetica, *Escherichia coli, Klebsiella oxytoca, Thermoanaerobacterium saccharolyticum, Yarrowia* sp., and *Bacillus* sp.

13. The method of claim 1, wherein the cell is selected from *Saccharomyces cerevisiae, Saccharomyces monacensis, Saccharomyces bayanus, Saccharomyces pastorianus, Saccharomyces carlsbergensis, Saccharomyces pombe, Trichoderma reesei, Neurospora crassa, Kluyveromyces marxiamus, Kluyveromyces lactis, Kluyveromyces fragilis, Pichia stipitis, Pichia pastoris, Sporotrichum thermophile, Candida shehatae, Candida tropicalis, Neurospora crassa, Zymomonas mobilis, Clostridium saccharoperbutylacetonicum, Clostridium phytofermentans, Clostridium thermocellum, Clostridium beijerinckii, Clostridium acetobutylicum, Clostridium botulinum, Clostridium butyricum, Clostridium diolis, Clostridium ljungdahlii, Clostridium aerotolerans, Clostridium cellulolyticum, Clostridium tyrobutyricum, Clostridium pasteurianum, Moorella thermoacetica, Escherichia coli, Klebsiella oxytoca, Thermoanaerobacterium saccharolyticum, Yarrowia lipolytica*, and *Bacillus subtilis.*

14. The method of claim 2, wherein the cell is selected from *Saccharomyces cerevisiae, Saccharomyces monacensis, Saccharomyces bayanus, Saccharomyces pastorianus, Saccharomyces carlsbergensis, Saccharomyces pombe, Trichoderma reesei, Neurospora crassa, Kluyveromyces marxiamus, Kluyveromyces lactis, Kluyveromyces fragilis, Pichia stipitis, Pichia pastoris, Sporotrichum thermophile, Candida shehatae, Candida tropicalis, Neurospora crassa, Zymomonas mobilis, Clostridium saccharoperbutylacetoni-* cum, *Clostridium phytofermentans, Clostridium thermocellum, Clostridium beijerinckii, Clostridium acetobutylicum, Clostridium botulinum, Clostridium butyricum, Clostridium diolis, Clostridium ljungdahlii, Clostridium aerotolerans, Clostridium cellulolyticum, Clostridium tyrobutyricum, Clostridium pasteurianum, Moorella thermoacetica, Escherichia coli, Klebsiella oxytoca, Thermoanaerobacterium saccharolyticum, Yarrowia lipolytica*, and *Bacillus subtilis*.

15. The method of claim 3, wherein the cell is selected from *Saccharomyces cerevisiae, Saccharomyces monacensis, Saccharomyces bayanus, Saccharomyces pastorianus, Saccharomyces carlsbergensis, Saccharomyces pombe, Trichoderma reesei, Neurospora crassa, Kluyveromyces marxiamus, Kluyveromyces lactis, Kluyveromyces fragilis, Pichia stipitis, Pichia pastoris, Sporotrichum thermophile, Candida shehatae, Candida tropicalis, Neurospora crassa, Zymomonas mobilis, Clostridium saccharoperbutylacetonicum, Clostridium phytofermentans, Clostridium thermocellum, Clostridium beijerinckii, Clostridium acetobutylicum, Clostridium botulinum, Clostridium butyricum, Clostridium diolis, Clostridium ljungdahlii, Clostridium aerotolerans, Clostridium cellulolyticum, Clostridium tyrobutyricum, Clostridium pasteurianum, Moorella thermoacetica, Escherichia coli, Klebsiella oxytoca, Thermoanaerobacterium saccharolyticum, Yarrowia lipolytica*, and *Bacillus subtilis*.

16. The method of claim 1 wherein the cell is further recombinantly engineered to express one or more proteins necessary for heme biosynthesis selected from the group consisting of uroporphyrinogen III decarboxylase, coproporphyrinogen III oxidase, protoporphyrinogen IX oxidase, and ferrochelatase.

17. The method of claim 1, wherein the treating step comprises producing the chlorite in the culture medium by electrochemical generation.

18. The method of claim 1, wherein the treating step is performed intermittently.

19. The method of claim 1 further comprising culturing the cell under conditions sufficient for the cell to produce a fermentation product.

20. The method of claim 1, wherein the treating step comprises directly adding the chlorite to the culture medium.

* * * * *